(12) United States Patent
Holländer

(10) Patent No.: US 8,796,028 B2
(45) Date of Patent: Aug. 5, 2014

(54) METHOD FOR TREATING A BIOLOGICAL SAMPLE WITH A COMPOSITION CONTAINING AT LEAST ONE POLYOL AND EXCLUDING WATER

(75) Inventor: Vera Holländer, Unna (DE)

(73) Assignee: Qiagen GmbH, Hilden (DE)

(*) Notice: Subject to any disclaimer, the term of this patent is extended or adjusted under 35 U.S.C. 154(b) by 904 days.

(21) Appl. No.: 12/087,167

(22) PCT Filed: Dec. 29, 2006

(86) PCT No.: PCT/EP2006/070267
§ 371 (c)(1),
(2), (4) Date: May 21, 2009

(87) PCT Pub. No.: WO2007/077199
PCT Pub. Date: Jul. 12, 2007

(65) Prior Publication Data
US 2010/0009349 A1    Jan. 14, 2010

(30) Foreign Application Priority Data
Dec. 30, 2005    (EP) .................................. 05028767

(51) Int. Cl.
G01N 1/30       (2006.01)
G01N 33/68      (2006.01)
C12Q 1/68       (2006.01)

(52) U.S. Cl.
USPC .................. 436/17; 436/18; 436/63; 436/176

(58) Field of Classification Search
USPC ........... 436/8, 17, 18, 63, 174, 176; 435/40.5, 435/40.52; 424/75; 422/1, 26, 32
See application file for complete search history.

(56) References Cited

U.S. PATENT DOCUMENTS

| | | | |
|---|---|---|---|
| 4,946,669 A | 8/1990 | Siegfried et al. | |
| 5,104,640 A | 4/1992 | Stokes | |
| 5,260,048 A * | 11/1993 | Ryan ............................. | 435/40.5 |
| 5,439,667 A * | 8/1995 | Camiener ..................... | 435/40.5 |
| 5,482,676 A * | 1/1996 | Camiener ..................... | 422/430 |
| 6,207,408 B1 | 3/2001 | Essenfeld et al. | |
| 6,929,782 B1 | 8/2005 | Ciliberto et al. | |
| 2003/0086830 A1 | 5/2003 | Haywood et al. | |
| 2005/0074422 A1 | 4/2005 | Visinoni | |
| 2005/0118725 A1* | 6/2005 | Towne et al. ................... | 436/174 |
| 2005/0195684 A1 | 9/2005 | Mayer | |

FOREIGN PATENT DOCUMENTS

| | | |
|---|---|---|
| CN | 1310797 A | 9/2001 |
| EP | 0311035 | 4/1989 |
| EP | 0338469 | 10/1989 |
| EP | 338469 A2 * | 10/1989 |
| EP | 1455174 | 9/2004 |
| JP | 57189698 | 11/1982 |
| JP | 1-199160 | 8/1989 |
| JP | 3-295465 | 12/1991 |
| JP | 7-507266 | 8/1995 |
| JP | 7-333219 | 12/1995 |
| JP | 2000-187033 | 7/2000 |
| JP | 2001/516869 | 10/2001 |
| JP | 2004-271497 | 9/2004 |
| JP | 2005-506526 | 3/2005 |
| JP | 2005-509870 | 4/2005 |
| JP | 2005-532030 | 10/2005 |
| WO | WO 93/05650 | 4/1993 |
| WO | WO 99/09390 | 2/1999 |
| WO | WO 00/00813 | 1/2000 |
| WO | WO 00/32252 | 6/2000 |
| WO | WO 03/031064 | 4/2003 |
| WO | WO03/031065 | 4/2003 |
| WO | WO 03/044213 | 5/2003 |

OTHER PUBLICATIONS

Matsubayashi, Hiroyuki et al. "Advantages of immunostaining over DNA analysis using PCR amplification to detect p53 abnormaility in long-term formalin-fixed tissues of human colorectal carcinomas." Journal of Gasterenterology (1998) 33 662-669.*
da Silva, Rosane Maria Guimares et al. "Preservation of cadavers for surgical technique training." Veterinary Science (2004) 33 606-608.*
Haag, D. et al. "Simultaneous differential staining of nucleic acids and proteins in histological tissues by means of J-band effect." Histochemie (1971) 26 190-193.*
O'Sullivan, E. et al. "An improved composition for embalming fluid to preserve cadavers for anatomy teaching in the United Kingdom." Journal of Anatomy (1993) 182 295-297.*
Warmington, Adrian R. et al. "Evaluation of ethanol-based fixatives as a substitute for formalin in diagnostic clinical laboratories." J. Histotech (2000) 23 299-308.* Parket, et al., "Storage of heart valve allografts in glycerol with subsequent antibiotic sterilization" Thorax, 1978, 33, 638-645.
Hubalek, "Protectants used in the cryopreservation of microorganisms" Cryobiology, 46 (2003), 205-229.
Kuhlmann, W.D. and Krischan, R., "Resin Embedment of Organs and Postembedment Localization of Antigens by Immunoperoxidase Methods," *Histochemistry* 72:377-389 (1981).

* cited by examiner

*Primary Examiner* — Christopher A Hixson
(74) *Attorney, Agent, or Firm* — Fanelli Haag & Kilger PLLC

(57) ABSTRACT

The invention relates to a method for treating a biological sample, comprising the following method steps: i) preparation of a biological sample and ii) bringing the biological sample into contact with a composition, comprising: (1) 1 to 100 wt. % of at least one polyol and (2) 0 to 99 wt. % of at least one additive, wherein the total amount of components (1) and (2) is 100 wt. %. The invention further relates to biological samples obtained by said method, a method for analysis of a treated biological sample, devices for treating a biological sample, use of said devices, various kits and use of a composition.

29 Claims, 10 Drawing Sheets

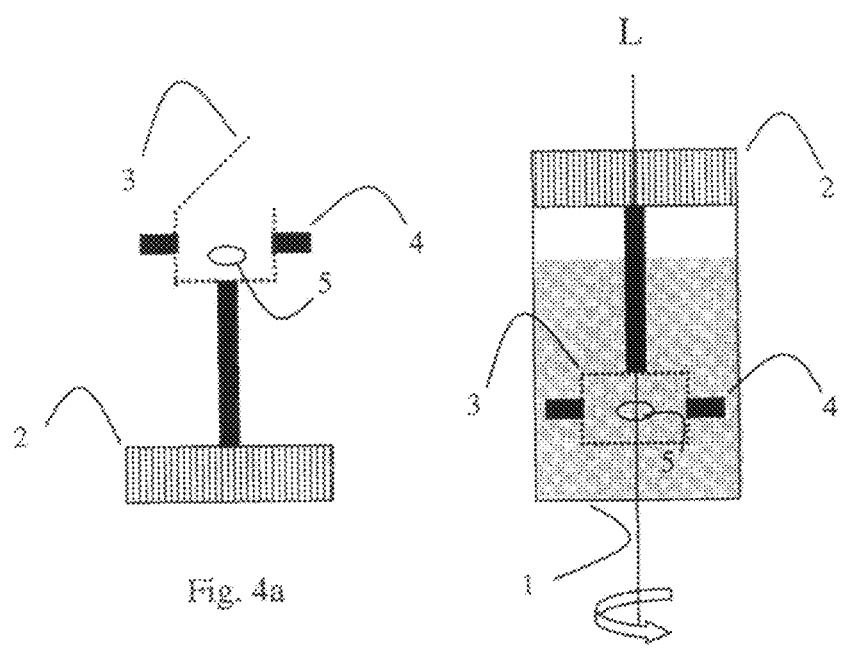
Fig. 4a
Fig. 4
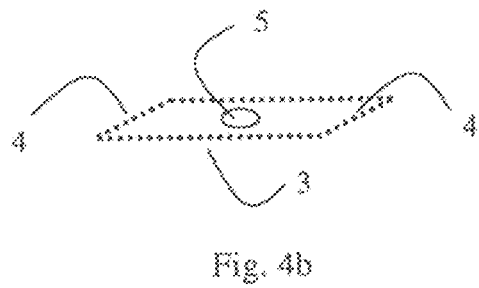
Fig. 4b 2-8°C/ERK2

25°C/actin

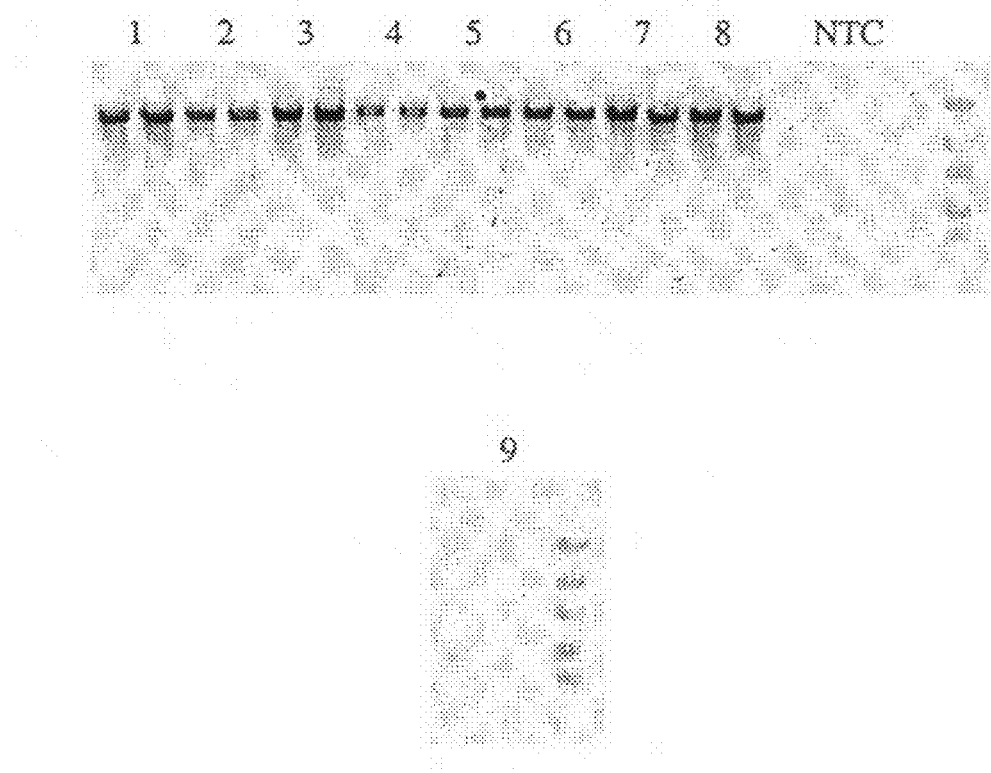

METHOD FOR TREATING A BIOLOGICAL SAMPLE WITH A COMPOSITION CONTAINING AT LEAST ONE POLYOL AND EXCLUDING WATER

CROSS-REFERENCE TO RELATED APPLICATIONS

This application is a United States national stage filing under 35 U.S.C.§371 of international (PCT) application No. PCT/EP2006/070267, filed Dec. 29, 2006 and designating the US, which claims priority to European application 05028767.1, filed Dec. 30, 2005.

FIELD OF THE INVENTION

The present invention relates to a method of treating a biological sample, to the biological sample obtainable by this method, to a method of analyzing a treated biological sample, to devices for treating a biological sample, to the use of these devices, to a variety of kits, and to the use of a composition.

BACKGROUND OF THE INVENTION

For a long time, scientists have focused only on the pathological and/or histological study of biological samples. A preservation and/or stabilization of the samples for such studies was usually carried out, if at all, by placing the samples into formaldehyde solutions and/or by embedding the samples in paraffin. But even the cooling or freezing of biological samples for preservation purposes has long been current practice.

Only when it was recognized that the detection of certain constituents of biological samples such as, for example, nucleic acids or proteins, is of great benefit, in particular in the field of medical and clinical diagnostics, did it become clear that novel, more effective and more economical preservation and/or stabilization reagents and/or methods were required.

In the course of these developments, one recognized that it is precisely the status (gene expression or protein pattern) of the fresh sample constituents which are important for molecular-biological study which may undergo rapid changes, even directly after the sample has been taken from its natural environment, so that even prolonged storage of the samples in the untreated state, for example as the result of unexpected delays during transport into the laboratory or the like, may falsify a molecular-biological analysis or indeed make the latter entirely impossible.

It is precisely the nucleic acid status of a biological sample which undergoes more rapid changes as more time elapses between sampling and the analysis of the sample. The ribonucleic acids (RNAs) in particular are degraded very rapidly as the result of ubiquitous RNases. Also, the degradation of nucleic acids is accompanied by the induction of, for example, stress genes and thus the synthesis of novel mRNA molecules which likewise greatly modify the transcription pattern of the sample. It is therefore necessary immediately to stabilize the sample in order to retain the gene expression profile to be analyzed.

An immediate stabilization of the sample is necessary not only for analyzing nucleic acids, but also for detailed proteomic studies of a biological sample since the protein pattern too undergoes changes immediately after sampling. This is the result firstly of degradation or de novo synthesis, but also changes in the protein modification, such as, for example, phosphorylation/dephosphorylation, which happens very rapidly.

Since protein-chemical and molecular-biological analyses are employed not only in the field of medical and clinical diagnostics, but also increasingly in other fields such as forensics, pharmacy, food analytics, agriculture, environmental analytics and in many research projects, retaining the integrity of the molecular structure of the samples, and, in this context, their immediate stabilization, is thus a prerequisite of utmost importance in all these fields.

Over the years, a multiplicity of very different stabilizing reagents and/or methods have been developed in order to stabilize a wide range of very different biological samples.

As already mentioned at the outset, it has long been known to stabilize samples by means of aqueous formaldehyde solution and subsequently embedding the stabilized samples for histological tissue studies. However, such a stabilization is in most cases unsuitable for the use of molecular-biological methods since the nucleic acids are only very insufficiently stabilized, which only makes possible a qualitative detection, at best, of the nucleic acids or nucleic acid fragments present, but not a quantitative detection. Moreover, the stabilization with crosslinking stabilizers such as aqueous formaldehyde solution leads to a reduced extractability of the nucleic acids or proteins from the tissues. Also, aqueous formaldehyde solution is not acceptable for toxicological reasons.

Stabilizing reagents such as, for example, the cationic detergents described in U.S. Pat. Nos. 5,010,184, 5,300,545, WO-A-02/00599 and WO-A-02/00600, which, in turn, give very good qualitative detection of the nucleic acids, are only suitable for samples which comprise single cells, or only one cell layer. To stabilize nucleic acids in compact pieces of tissue, however, such stabilizing reagents are not sufficient.

Moreover, those reagents and methods with which nucleic acids can be stabilized for the purposes of qualitative detection are, as a rule, not suitable for the simultaneous stabilization of proteins. Moreover, samples stabilized in this manner cannot be used for histological study since the stabilizer preserves for example the nucleic acids, but not the cell or tissue structures. Yet other stabilizing reagents which comprise, for example, highly concentrated ammonium sulfate (see, for example, U.S. Pat. No. 6,204,375) are well suited to the stabilization of nucleic acids in different tissues. However, they are largely unsuitable for use in the stabilization of cell-containing or cell-free body fluids such as, for example, blood, serum or plasma, and also have not as good stabilizing properties in some types of tissue, such as, for example, fatty tissue.

All the above shows that it is particularly difficult simultaneously to stabilize RNA, DNA and proteins in tissue samples and histologically to preserve the tissue samples. Moreover, work carried out on cells or other biological samples cannot necessarily be applied to compact tissue. In comparison with other biological samples, the stabilization of nucleic acids in compact tissue samples involves one particular difficulty. Tissues are composed of several layers and are heterogeneous with regard to their composition, their constituents and their structure. To stabilize nucleic acids in compact tissue samples, the stabilizing reagent must act not only on the cell surface, or within one cell layer, but also deep inside the multi-layer sample material. Moreover, one frequently has to address, within one and the same biological sample, very different types of tissue and/or cells, which differ for example with regard to their cell structure, the membrane construction, the compartmentalizations and the biomolecules, for example with regard to the proteins, the carbohydrates and/or the fat content.

One form of stabilizing tissue samples, including all constituents, which is known in the prior art and used very frequently is to freeze or deep-freeze the samples. Here, the sample is frozen in its natural environment in liquid nitrogen at below −80° C., immediately after having been taken. The sample treated thus can then be stored virtually indefinitely at approximately −70° C., without any changes in its integrity taking place. However, all such methods require very complicated logistic requirements since defrosting of the samples during transport, storage or during a wide range of purposes and utilizations must be prevented. Besides the additional costs for specific sample receptacles and for the permanent cooling of the samples, the use of liquid nitrogen is not only very complicated, but also can only be carried out with specific precautionary measures.

Moreover, a subsequent analysis of the frozen sample material, in particular individual components of the sample, is usually a very difficult endeavor. For example, defrosting, or incipient defrosting, of the sample during storage, transport or methoding leads to the degradation of, in particular, the RNA. This means that samples which have been subjected to defrosting, or incipient defrosting, no longer give reproducible results. In addition, it is precisely tissue pieces in the frozen state which are very difficult to method, for example divide, manually, or only with complex technical equipment.

Solutions referred to as transition solutions have also been described for lessening the disadvantages of methoding frozen samples, in particular for isolating RNA. Here, the frozen tissue is first transferred into a solutions precooled to −70° C. to −80° C., where it is stored for several hours (at least 16 hours) at approximately −20° C. Thereafter, the sample which is impregnated with the transition solution may be warmed to working temperatures of from −4° C. up to room temperature, for a brief period only, for example no longer than is necessary for dividing the sample, without any changes taking place in the nucleic acid status of the sample. However, further analyses, and storage of the sample, in particular at room temperature, are not possible. Such transition solutions which are known for example from WO-A-2004/72270 consist predominantly of monohydric alcohols.

The disadvantage of the samples treated with customary transition solutions is that they only remain stable at room temperature over a very short period, which means that the methoding time is only very limited and very readily exceeded in particular when methoding a large number of samples, in particular when cutting and chopping procedures are involved. Moreover, the transition is only very slow, whereby no direct experiments may follow, and waiting times of in most cases one day result. Equally, transport of the samples treated thus is not possible at room temperature without the sample being damaged, since not only must the transition take place at temperatures of ≤−20° C., but this must be followed by stable storage of the sample. Also, the transport of the sample is only possible at ≤−20° C., which requires the use of cooling means, for example dry ice, during transport. Furthermore, it must be taken into consideration that the monohydric alcohols employed in WO-A-2004/72270, such as, for example, methanol, ethanol or isopropanol, are readily flammable, volatile or toxic, and that, accordingly, certain safety precautions must be in place when using them.

While the use of the traditional transition solutions leads to improvements in sample methoding, such as, for example, chopping or cutting to size, they neither reduce the equipment requirements (since the solution for transition must be precooled at −70 to −80° C., and therefore still requires a suitable cooling device), nor is it possible to stabilize the transition-solution-treated samples at room temperature over a prolonged period.

The present invention was based on the object of overcoming the disadvantages of the prior art.

SUMMARY OF THE INVENTION

In particular, the present invention was based on the object of providing a method of stabilizing a biological sample which, with the use of the smallest possible amounts, if any, of readily flammable, volatile, carcinogenic, teratogenic, environmentally hazardous or toxic substances leads to a satisfactory stabilization of the biological sample.

Furthermore, the present invention was based on the object of providing a method of stabilizing a biological sample by means of which both frozen and fresh biological samples can be stabilized at moderate temperatures, as far as possible, for example also at room temperature, without adversely affecting the expression profile or the proteome of the biological sample.

Moreover, the method of stabilizing a biological sample should make possible both a histological analysis of the stabilized biological sample and an analysis of the biomolecules present in the biological sample. In this context, the stabilization method should make possible, in particular, the qualitative and quantitative analysis of both proteins and nucleic acids in the stabilized biological sample. Moreover, the stabilization of the biological sample should not, or if, then only slightly, adversely affect the quality of the nucleic acids which can be determined for example by gel analysis or by the number of the PCR cycles until a certain amount of nucleic acid has been obtained, and the quality of the proteins which, for example, in the case of an enzyme, can be determined by suitable activity assays.

Moreover, the method of stabilizing a biological sample should result in a stabilized biological sample which cannot only be analyzed at moderate temperatures, for example at room temperature, but which, if appropriate, can also be stored at such moderate temperatures for as long as possible before or after such an analysis. In the case of biomolecules, the term "stabilization" is understood as meaning the inhibition of the degradation, the modification, the induction or the change in the activity of the biomolecules. In the case of histological analyses of the biological samples, the term "stabilization" is preferably understood as meaning preventing a substantial change in sample morphology.

Furthermore, the present invention was based on the object of providing a device by means of which a biological sample can be stabilized in a simple manner, using the stabilization method according to the invention.

A method which contributes to achieving the objects mentioned at the outset is a method of treating a biological sample, comprising the method steps
i) providing a biological sample, and
ii) bringing the biological sample in contact with a composition comprising
 (α1) 1 up to 100% by weight, particularly preferably at least 5% by weight, more preferably at least 10% by weight, even more preferably at least 25% by weight, especially preferably at least 35% by weight and most preferably at least 50% by weight, for example at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% by weight, of at least one polyol, and (α2) 0 to 99% by weight, preferably 0 to 95% by weight, particularly preferably 0.1 to 50% by weight, even more preferably 0.5 to 25% by weight, more preferably 1 to 15% by weight and most preferably 2.5 to 10% by weight, for example up to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or 99% by weight, of at least one additive, where the total of components (α1) and (α2) amounts to 100% by weight.

BRIEF DESCRIPTION OF THE DRAWINGS

FIGS. 1a and 1b show a cross-section of two mixing devices (β4) with guide vanes of different designs, which are arranged below the immersion aid (β3).

FIG. 4 shows a lateral view of an embodiment of the first device according to the invention, where the immersion aid (β3) comprises a sample receptacle and where the mixing device (β4) is a component of the immersion aid (β3). FIG. 4a shows a lateral view of the immersion aid (β3) which is connected to the lid. FIG. 4b shows an immersion aid (β3) which is designed such that it has oblique side panels as guide vanes.

FIGS. 10 and 10a show the results of the analysis of the activity of a protein stabilized according to the invention (the reverse transcriptase "Omniscript" from QIAGEN), which has been carried out in example 8, in the form of an agarose-TAE gel made after PCR reaction.

DETAILED DESCRIPTION OF THE INVENTION

Figure 1:
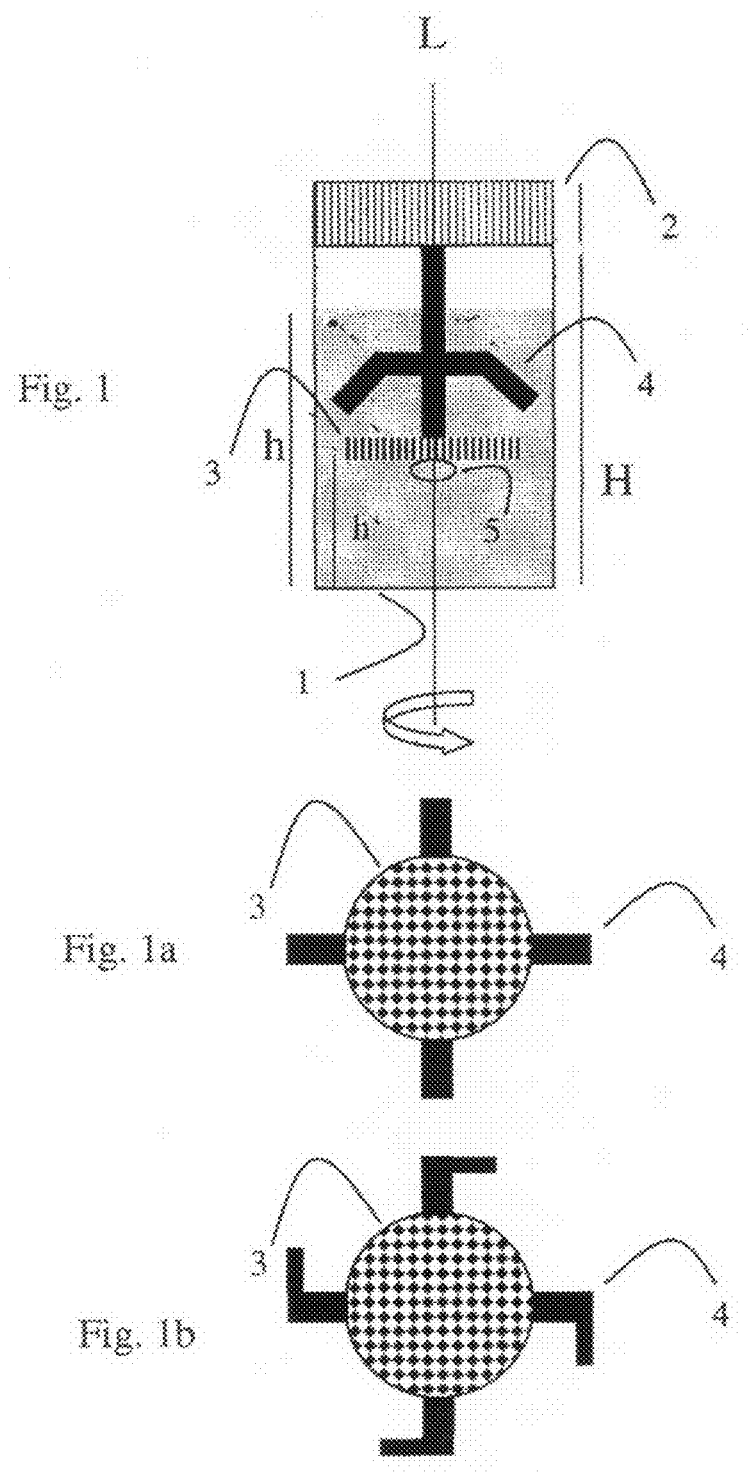
FIG. 1 shows a lateral view of an embodiment of the first device according to the invention, in which the mixing device (β4) is arranged above the immersion aid (β3).

Surprisingly, it has been found that freshly isolated biological samples can be stabilized, and frozen biological samples, for example biological samples which have been frozen in liquid nitrogen, can be prepared for histological or molecular-biological analysis, by means of polyol-containing compositions. Here, it is not necessary to cool the biological sample which has been brought into contact with the composition to temperatures of below 0° C. and to store or analyze it at such low temperatures, so that the method according to the invention can be carried out without complicated equipment, in particular without cooling devices or cooling means.

The biological sample provided in method step i) may take the form of a frozen or a nonfrozen biological sample, with the biological sample employed being any biological sample known to the skilled worker. Preferred biological samples are selected from the group comprising biomolecules, for example natural, preferably isolated linear, branched or circular nucleic acids such as RNA, in particular mRNA, siRNA, miRNA, snRNA, tRNA, hnRNA, or ribozymes, DNA and the like, synthetic or modified nucleic acids, for example oligonucleotides, in particular primers, probes or standards used for PCR, digoxigenin-, biotin- or fluorescent-labeled nucleic acids, or what are known as PNAs ("peptide nucleic acids"), natural, preferably isolated proteins or oligopeptides, synthetic or modified proteins or oligopeptides, for example antibodies coupled with fluorescent labels or with enzymes, or hormones, growth factors, lipids, oligosaccharides, polysaccharides, carbohydrates, proteoglucans, body fluids such as blood, sperm, cerebrospinal fluid, saliva, sputum or urine, liquids which are obtained when methoding blood, such as serum or plasma, leukocyte fractions or "buffy coat", leech saliva, fecal matter, smears, tap fluids, dandruff, hairs, skin fragments, forensic samples, food or environmental samples, which comprise free or bound biomolecules, in particular free or bound nucleic acids, or metabolic products and metabolites, intact organisms, preferably intact nonlive organisms, tissue of multi-celled organisms, preferably from insect and mammals, in particular from humans, for example in the form of tissue sections, tissue fragments or organs, isolated cells, for example in the form of anchorage-dependent or suspended cell cultures, organelles, for example chloroplasts or mitochondria, vesicles, nuclei or chromosomes, plants, plant parts, plant tissue or plant cells, bacteria, viruses, viroids, prions, yeast and fungi or parts of fungi.

The nonfrozen biological sample which is employed in method step i) of the method according to the invention is preferably a freshly prepared biological sample, for example a fresh tissue sample or freshly isolated blood cells from a live or dead organism or, in the case of synthetic biomolecules as biological sample, freshly synthetized nucleic acids or proteins. In this context, a "fresh" biological sample is preferably understood as meaning, according to the invention, a sample which has been taken no longer than 96 hours, preferably no longer than 48 hours, particularly preferably no longer than 24 hours, more preferably no longer than 10 hours, especially preferably no longer than 60 minutes and most preferably no longer than 10 minutes, or, in the case of a synthetic biomolecule, which has been synthetized no longer than 96 hours, preferably no longer than 48 hours, particularly preferably no longer than 24 hours, more preferably no longer than 10 hours, especially preferably no longer than 60 minutes and most preferably no longer than 10 minutes before being brought into contact with the composition in method step ii). However, the term "fresh" biological sample also comprises those samples which have been taken within the above periods of time, but which have also been pretreated before being brought into contact with the composition, for example with conventional fixatives such as aqueous formaldehyde solution, with dyes, such as eosin, with antibodies and the like. In this context, the preparation of fresh cell or tissue samples can be effected by all preparation methods known to the skilled worker for this purpose, in the case of a tissue sample for example by means of a surgical blade, such as during an operation or a post-mortem, in the case of a blood cell sample by centrifugation of freshly taken blood, and the like. When a fresh biological sample is employed, the composition which is employed in method step ii) serves mainly as stabilizing composition.

The frozen biological sample which is employed in method step i) of the method according to the invention is preferably a biological sample which, after having been isolated in the above described manner, has first been cooled to temperatures of 0° C. or less, preferably to temperatures of −20° C. or less and most preferably to temperatures of −70° C. or less, for example by bringing into contact with liquid nitrogen, before being brought into contact with the composition in method step ii). If a biological sample which has been frozen in this manner is employed in the method according to the invention, the composition which is employed in method step ii) serves mainly as transition composition.

The polyol ($\alpha$1) which is present in the composition preferably takes the form of a diol, triol, tetraol, pentaol, hexaol, heptaol, octaol or nonaol, with a diol, triol, tetraol, pentaol or hexaol being particularly preferred, a diol and a triol being more preferred and a triol being most preferred.

Furthermore, it is preferred according to the invention for the polyol ($\alpha$1) to have 2 to 20 carbons and, accordingly, to be a C2-polyol, a C3-polyol, a C4-polyol, a C5-polyol, a C6-polyol, a C7-polyol, a C8-polyol, a C9-polyol, C10-polyol, a C11-polyol, a C12-polyol, a C13-polyol, C14-polyol, a C15-polyol, a C16-polyol, a C17-Polyol, C18-polyol, a C19-polyol or a C20-Polyol. Particularly preferred, however, is a polyol having 2 to 12 carbon atoms, that is to say a C2-polyol, a C3-polyol, a C4-polyol, a C5-polyol, C6-polyol, a C7-polyol, a C8-polyol, a C9-polyol, C10-polyol, a C11-polyol or a C12-polyol, and most preferably a polyol having 2 to 6 carbon atoms, that is to say a C2-polyol, a C3-polyol, a C4-polyol, a C5-polyol, C6-polyol.

In principle, the polyols may be straight-chain, branched or cyclic. In the case of a linear or branched polyol, it may be particularly advantageous for the polyols to have an OH group attached at each of the ends of the longest hydrocarbon chain in the molecule.

In accordance with a particularly preferred embodiment of the composition employed in the method according to the invention, the composition comprises, as polyol ($\alpha$1), a polyol which has a melting point above 0° C., particularly preferably above 5° C., more preferably above 10° C., especially preferably above 15° C. and most preferably above 20° C., the melting point preferably being determined in a capillary by means of a Lindstroem melting-point apparatus.

Polyols which are particularly suitable according to the invention are selected, but not limited to polyols, from the group comprising 1,2-ethanediol, 1,2-propanediol, 1,3-propanediol, 2-methyl-1,3-propanediol, 2-methyl-1,2-propanediol, 2,2-dimethyl-1,3-propanediol, 2,2-diethyl-1,3-propanediol, 2-methyl-2-propyl-1,3-propanediol, 2-butyl-2-ethyl-1,3-propanediol, dihydroxyacetone, 2,2-dibutyl-1,3-propanediol, 3-methoxy-1,3-propanediol, 3-methoxy-1,2-propanediol, 3-methoxy-2,3-propanediol, 2-methoxymethyl-1,3-propanediol, 3-ethoxy-1,3-propanediol, 3-ethoxy-1,2-propanediol, 3-ethoxy-2,3-propanediol, 3-allyloxy-1,2-propanediol, 1,2-butanediol, 1,3-butanediol, 1,4-butanediol, 2,3-butanediol, 2,3-dimethyl-2,3-butanediol, 3,3-dimethyl-1,2-butanediol, 1,2-pentanediol, 1,3-pentanediol, 1,4-pentanediol, 1,5-pentanediol, 2,3-pentanediol, 2,4-pentanediol, 2-methyl-2,4-pentanediol, 2,4-dimethyl-2,4-pentanediol, 2,2,4-trimethyl-1,3-pentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, 2,5-dimethyl-2,5-hexanediol, 2-ethyl-1,3-hexanediol, 1,2-heptanediol, 1,3-heptanediol, 1,4-heptanediol, 1,5-heptanediol, 1,6-heptanediol, 1,7-heptanediol, 1,8-octanediol, 1,2-octanediol, 1,3-octanediol 1,4-octanediol, 1,5-octanediol, 1,6-octanediol, 1,7-octanediol, 1,2-nonadiol, 1,9-nonadiol, 1,10-decanediol, 1,2-decanediol, 1,2-undecanediol, 1,11-undecanediol, 1,12-dodecanediol, 1,2-dodecanediol, diethylene glycol, dipropylene glycol, triethylene glycol, tripropylene glycol, tetraethylene glycol, tetrapropylene glycol, pentaethylene glycol, pentapropylene glycol, hexaethylene glycol, hexapropylene glycol, heptaethylene glycol, heptapropylene glycol, octaethylene glycol, octapropylene glycol, nonaethylene glycol, nonapropylene glycol, decaethylene glycol, decapropylene glycol, cis- or trans-1,2-cylopentanediol, cis- or trans-1,3-cylopentanediol, cis- or trans-1,2-cylohexanediol, cis- or trans-1,3-cylohexanediol, cis- or trans-1,4-cylohexanediol, cis- or trans-1,2-cyloheptanediol, cis- or trans-1,3-cyloheptanediol, cis- or trans-1,4-cyloheptanediol, 1,2,3-cyclopentanetriol, 1,2,4-cyclopentanetriol, 1,2,3-cyclohexanetriol, 1,2,4-cyclohexanetriol, 1,2,3-cyloheptanetriol, 1,2,4-cyloheptanetriol, 1,2,3-propanetriol, 3-ethyl-2-hydroxymethyl-1,3-propanediol, 2-hydroxymethyl-2-methyl-1,3-propanediol, 2-hydroxymethyl-2-methyl-1,3-propanediol, 1,2,3-butanetriol, 1,2,4-butanetriol, 2-methyl-1,2,3-butanetriol, 2-methyl-1,2,4-butanetriol, 1,2,3-pentanetriol, 1,2,4-pentanetriol, 1,2,5-pentanetriol, 2,3,4-pentanetriol, 1,3,5-pentanetriol, 3-methyl-1,3,5-pentanetriol, 1,2,3-hexanetriol, 1,2,4-hexanetriol, 1,2,5-hexanetriol, 1,2,6-hexanetriol, 2,3,4-hexanetriol, 2,3,5-hexanetriol, 1,2,3-heptanetriol, 1,2,7-heptanetriol, 1,2,3-octanetriol, 1,2,8-octanetriol, 1,2,3-nonatriol, 1,2,9-nonatriol, 1,2,3-decanetriol, 1,2,10-decanetriol, 1,2,3-undecanetriol, 1,2,11-undecanetriol, 1,2,3-dodecanetriol, 1,1,12-dodecanetriol, 2,2,-bis(hydroxymethyl)-1,3-propanediol, 1,2,3,4-butanetetraol, 1,2,3,4-pentanetetraol, 1,2,3,5-pentanetetraol, 1,2,3,4-hexanetetraol, 1,2,3,6-hexanetetraol, 1,2,3,4-heptanetetraol, 1,2,3,7-heptanetetraol, 1,2,3,4-octanetetraol, 1,2,3,8-octanetetraol, 1,2,3,4-nonanetetraol, 1,2,3,9-nonanetetraol, 1,2,3,4-decanetetraol, 1,2,3,10-decanetetraol, trimethylolpropanol, pentaerythritol, sugar alcohols such as mannitol, sorbitol or arabitol, hexanehexol, 1,2,3,4,5-pentanepentol and 1,2,3,4,5,6-hexanehexaol.

In the composition according to the invention, the polyols may be present individually or in the form of a mixture of two, three, four or five different polyols, with mixtures of two different diols, mixtures of two different triols, mixtures of two different tetraols, mixtures of one diol and one triol, mixtures of one diol and one tetraol and mixtures of one triol and one tetraol being particularly preferred and mixtures of two different triols being most preferred as polyol mixtures.

The additive ($\alpha$2) which was optionally present in the composition may take the form of further solvents other than polyols or of an additive which is selected from the group comprising detergents, inhibitors which inhibit the degradation of nucleic acids or proteins, such as, for example, the protease inhibitor PMSF or the commercially available products ANTI-RNase (Ambion, St. Austin, USA), RNAsecure® (Ambion) or DEPC, alkylating agents, acetylating agents, halogenating agents, nucleotides, nucleotide analogs, amino acids, amino acid analogs, viscosity regulators, colorants, in particular colorants for specifically staining certain cell structures, buffer compounds, for example HEPES, MOPS or TRIS, preservatives, complexing agents such as, for example, EDTA or EGTA, reducing agents such as, for example, 2-mercaptoethanol, dithiothreitol (DTT), pterine, hydrogen sulfide, ascorbic acid, NADPH, tricarboxyethylphosphine (TCEP) and hexamethylphosphoric triamide (Me2N)3P, oxidants such as 5,5'-dithiobis(2-nitrobenzoic acid) (DTNB), substances which improve cell permeability, for example DMSO or DOPE, chaotropic substances such as, for example, guanidinium isothiocyanate or guanidinium hydrochloride, fixatives such as, for example, formaldehyde or glutardialdehyde, crosslinking additives such as, for example, para-formaldehyde, and mixtures of at least two, at least three, at least four, at least five or at least six of these additives.

The solvent which is other than a polyol may take the form of water, or else an organic solvent other than a polyol, which is preferably selected from the group comprising monohydric alcohols (monools), ketones, dimethyl sulfoxide, aromatic hydrocarbons, halogenated hydrocarbons, ethers, carboxylic acids, carboxamides, nitriles, nitroalkanes and esters, with it being possible for suitable solvents to be selected for example from the group consisting of methanol, ethanol, 1-propanol, 2-propanol, acetonitrile, acetone, anisole, benzonitrile, 1-methoxy-2-propanol, quinoline, cyclohexanone, diacetin, dichloromethane, chloroform, diethyl ether, dimethyl ether, toluene, dimethyl ketone, diethyl ketone, dimethyl adipate, dimethyl carbonate, dimethyl sulfite, dioxane, dimethyl sulfoxide, methyl acetate, ethyl acetate, benzoic acid, methyl benzoate, ethyl benzoate, ethylbenzene, formamide, glycerol triacetate, ethyl acetoacetate, methyl acetoacetate, N,N-diethylacetamide, N-methyl-N-ethylacetamide, N,N-dimethylacetamide, N,N-dimethylformamide, N-methyl-N-ethylformamide, N,N-diethylformamide, N,N-dimethylthioformamide, N,N-diethylthioformamide, N-methyl-N-ethylthioformamide, N,N-dimethylacetamide, N-methyl-N-ethylacetamide, N,N-diethylacetamide, nitroethane, nitromethyltoluene and triethyl phosphate.

The composition of components (α1) and (α2) is preferably prepared by simply mixing the two components. In the event that the polyol (α1) has a melting point above room temperature, it may be preferable to heat the polyol to melting point and then to mix it with the additive. However, in the event that one of the components (α1) or (α2) is in solid form and one component in liquid form when the composition is prepared, it is also feasible to dissolve the solid component in the liquid component. Thus, for example, a solid polyol may be dissolved in liquid additive, or a solid additive may be dissolved in liquid polyol.

Compositions which are suitable in accordance with the invention are, for example, the compositions (all percentages unless otherwise stated are by volume. Furthermore, all percentages by volume of the individual components relate to the amount of the corresponding compound in one of the commercially available maximum concentrations, unless otherwise stated): 5% N,N-dimethylacetamide+10% methanol+20% acetone+25% DMSO+40% diethylene glycol, 25% 1,2-propanediol+75% acetone, 25% 1,2-propanediol+75% diethylene glycol, 25% 1,2-propanediol+75% DMSO, 25% 1,2-propanediol+75% ethanol, 25% 1,2-propanediol+75% ethylene glycol, 25% 1,3-propanediol+75% 1,2-propanediol, 25% 1,3-propanediol+75% acetone, 25% 1,3-propanediol+75% diethylene glycol, 25% 1,3-propanediol+75% DMSO, 25% 1,3-propanediol+75% ethanol, 25% 1,3-propanediol+75% ethylene glycol, 25% acetone+75% methanol, 25% diethylene glycol+75% acetone, 25% diethylene glycol+75% DMSO, 25% diethylene glycol+75% ethanol, 25% diethylene glycol+75% methanol, 25% diethylene glycol+75% N,N-dimethylacetamide, 25% dihydroxyacetone+75% 1,2-propanediol, 25% dihydroxyacetone+75% 1,3-propanediol, 25% dihydroxyacetone+75% diethylene glycol, 25% dihydroxyacetone+75% ethylene glycol, 25% dihydroxyacetone+75% triethylene glycol, 25% ethylene glycol+75% diethylene glycol, 25% ethylene glycol+75% DMSO, 25% ethylene glycol+75% ethanol, 25% 1,2,3-propanetriol+75% 1,2-propanediol, 25% 1,2,3-propanetriol+75% 1,3-propanediol, 25% 1,2,3-propanetriol+75% diethylene glycol, 25% 1,2,3-propanetriol+75% dihydroxyacetone, 25% 1,2,3-propanetriol+75% DMSO, 25% 1,2,3-propanetriol+75% ethylene glycol, 25% 1,2,3-propanetriol+75% N,N-diethylacetamide, 25% 1,2,3-propanetriol+75% triethylene glycol, 25% N,N-diethylacetamide+75% 1,3-propanediol, 25% N,N-diethylacetamide+75% 1,2-propanediol, 25% N,N-diethylacetamide+75% diethylene glycol, 25% N,N-diethylacetamide+75% ethylene glycol, 25% N,N-diethylacetamide+75% triethylene glycol, 25% triethylene glycol+75% 1,2-propanediol, 25% triethylene glycol+75% 1,3-propanediol, 25% triethylene glycol+75% acetone, 25% triethylene glycol+75% diethylene glycol, 25% triethylene glycol+75% DMSO, 25% triethylene glycol+75% ethanol, 25% triethylene glycol+75% ethylene glycol, 50% N,N-diethylacetamide+50% 1,3-propanediol, 50% 1,2-propanediol+50% acetone, 50% 1,2-propanediol+50% diethylene glycol, 50% 1,2-propanediol+50% DMSO, 50% 1,2-propanediol+50% ethanol, 50% 1,2-propanediol+50% ethylene glycol, 50% 1,3-propanediol+50% 1,2-propanediol, 50% 1,3-propanediol+50% acetone, 50% 1,3-propanediol+50% diethylene glycol, 50% 1,3-propanediol+50% DMSO, 50% 1,3-propanediol+50% ethanol, 50% 1,3-propanediol+50% ethylene glycol, 50% diethylene glycol+50% acetone, 50% diethylene glycol+50% DMSO, 50% diethylene glycol+50% methanol, 50% diethylene glycol+50% N,N-dimethylacetamide, 50% dihydroxyacetone+50% 1,2-propanediol, 50% dihydroxyacetone+50% 1,3-propanediol, 50% dihydroxyacetone+50% diethylene glycol, 50% dihydroxyacetone+50% ethanol, 50% dihydroxyacetone+50% ethylene glycol, 50% dihydroxyacetone+50% triethylene glycol, 50% ethylene glycol+50% acetone, 50% ethylene glycol+50% diethylene glycol, 50% ethylene glycol+50% DMSO, 50% ethylene glycol+50% ethanol, 50% 1,2,3-propanetriol+50% 1,2-propanediol, 50% 1,2,3-propanetriol+50% 1,3-propanediol, 50% 1,2,3-propanetriol+50% diethylene glycol, 50% 1,2,3-propanetriol+50% dihydroxyacetone, 50% 1,2,3-propanetriol+50% DMSO, 50% 1,2,3-propanetriol+50% ethylene glycol, 50% 1,2,3-propanetriol+50% N,N-diethylacetamide, 50% 1,2,3-propanetriol+50% triethylene glycol, 50% N,N-diethylacetamide+50% 1,2-propanediol, 50% N,N-diethylacetamide+50% diethylene glycol, 50% N,N-diethylacetamide+50% ethylene glycol, 50% N,N-diethylacetamide+50% triethylene glycol, 50% triethylene glycol+50% 1,2-propanediol, 50% triethylene glycol+50% 1,3-propanediol, 50% triethylene glycol+50% acetone, 50% triethylene glycol+50% diethylene glycol, 50% triethylene glycol+50% DMSO, 50% triethylene glycol+50% ethanol, 50% triethylene glycol+50% ethylene glycol, 75% 1,2-propanediol+25% acetone, 75% 1,2-propanediol+25% diethylene glycol, 75% 1,2-propanediol+25% DMSO, 75% 1,2-propanediol+25% ethanol, 75% 1,2-propanediol+25% ethylene glycol, 75% 1,3-propanediol+25% 1,2-propanediol, 75% 1,3-propanediol+25% acetone, 75% 1,3-propanediol+25% diethylene glycol, 75% 1,3-propanediol+25% DMSO, 75% 1,3-propanediol+25% ethanol, 75% 1,3-propanediol+25% ethylene glycol, 75% diethylene glycol+25% acetone, 75% diethylene glycol+25% DMSO, 75% diethylene glycol+25% methanol, 75% diethylene glycol+25% N,N-dimethylacetamide, 75% dihydroxyacetone+25% ethanol, 75% dihydroxyacetone+25% 1,2-propanediol, 75% dihydroxyacetone+25% 1,3-propanediol, 75% dihydroxyacetone+25% diethylene glycol, 75% dihydroxyacetone+25% ethylene glycol, 75% dihydroxyacetone+25% triethylene glycol, 75% ethylene glycol+25% acetone, 75% ethylene glycol+25% diethylene glycol, 75% ethylene glycol+25% DMSO, 75% 1,2,3-propanetriol+25% 1,2-propanediol, 75% 1,2,3-propanetriol+25% 1,3-propanediol, 75% 1,2,3-propanetriol+25% diethylene glycol, 75% 1,2,3-propanetriol+25% dihydroxyacetone, 75% 1,2,3-propanetriol+25% DMSO, 75% 1,2,3-propanetriol+25% ethanol, 75% 1,2,3-propanetriol+25% ethylene glycol, 75% 1,2,3-propanetriol+25% N,N-diethylacetamide, 75% 1,2,3-propanetriol+25% triethylene glycol, 75% N,N-diethylacetamide+25% 1,3-propanediol, 75% N,N-diethylacetamide+25% 1,2-propanediol, 75% N,N-diethylacetamide+25% diethylene glycol, 75% N,N-diethylacetamide+25% ethylene glycol, 75% N,N-diethylacetamide+25% triethylene glycol, 75% triethylene glycol+25% 1,2-propanediol, 75% triethylene glycol+25% 1,3-propanediol, 75% triethylene glycol+25% acetone, 75% triethylene glycol+25% diethylene glycol, 75% triethylene glycol+25% DMSO, 75% triethylene glycol+25% ethanol, 75% triethylene glycol+25% ethylene glycol, 90% 1,3-propanediol+10% methanol, 90% dihydroxyacetone+10% methanol, 90% ethylene glycol+10% methanol, 90% 1,2,3-propanetriol+10% methanol, 90% triethylene glycol+10% methanol, 95% 1,2-propanediol+5% N,N-dimethylacetamide, 95% 1,3-propanediol+5% N,N-dimethylacetamide, 95% ethylene glycol+5% N,N-dimethylacetamide, 95% 1,2,3-propanetriol+5% N,N-dimethylacetamide, 95% triethylene glycol+5% N,N-dimethylacetamide, ≥96% by weight 1,2,6-hexanetriol, ≥99.5% by weight 1,2,3-propanetriol, ≥80% by weight 3-methyl-1,3,5-pentanetriol, ≥90% by weight 1,2,4-butanetriol, 75% 1,2,3-propanetriol+25% 1,2,6-hexanetriol (96% by weight strength), 50% 1,2,3-propanetriol+50% 1,2,6-hexanetriol (96% by weight strength), 25% 1,2,3-propanetriol+75% 1,2,6-hexanetriol (96% by weight strength), 75% 1,2,3-propanetriol+25% 3-methyl-1,3,5-pentanetriol (80% by weight strength), 50% 1,2,3-propanetriol+50% 3-methyl-1,3,5-pentanetriol (80% by weight strength), 25% 1,2,3-propanetriol+75% 3-methyl-1,3,5-pentanetriol (80% by weight strength), 75% 1,2,6-hexanetriol (96% by weight strength)+25% 3-methyl-1,3,5-pentanetriol (80% by weight strength), 50% 1,2,6-hexanetriol (96% by weight strength)+50% 3-methyl-1,3,5-pentanetriol (80% by weight strength), 25% 1,2,6-hexanetriol (96% by weight strength)+75% 3-methyl-1,3,5-pentanetriol (80% by weight strength), 4.72M 1,2,3,4,5,6-hexanehexaol and ,2,3,4,5-pentanepentol (saturated solution in water).

The bringing into contact of the composition with the biological sample in method step ii) is preferably effected by immersing the biological sample in the composition which, upon the bringing-into contact operation, is preferably present in liquid form, so that the entire sample can be impregnated with the composition. If a fluid or isolated cells or for example a granular sample is employed as the biological sample, the bringing into contact is effected by mixing the biological sample with the composition or by suspending the biological sample in the composition. As an alternative, compositions which are solid at the chosen temperature may be dissolved directly in a liquid biological sample (for example blood, plasma, urine, saliva).

It is furthermore preferred that the composition during the bringing-into-contact operation with the biological sample is present in fluid, particularly preferably in liquid form, where the viscosity, determined at 20° C., of the composition is usually in a range of from 1 to 1 000 000 mPas, preferably in a range of from 1 to 100 000 mPas and particularly preferably in a range of from 1 to 10 000 mpas. As an alternative, however, the composition may also be solid and brought into contact with a liquid biological sample.

In accordance with a particular embodiment of the method according to the invention, it is preferred that the bringing into contact of the biological sample with the composition is carried out at a temperature in a range of from −80° C. to +80° C., preferably in a range of from 0° C. to +80° C., even more preferably in a range of from 2, 3, 4, 5, 6, 7 or 8° C. to +80° C. and more preferably in a range of from 18° C. to +80° C., for example at a temperature of at least −20° C., −19° C., −18° C., −17° C., −16° C., −15° C., −14° C., −13° C., −12° C., −11° C., −10° C., −9° C, −8° C., −7° C., −6° C., −5° C., −4° C., −3° C., −2° C., −1° C., 0° C., 1° C., 2° C., 3° C., 4° C., 5° C. 6° C., 7° C., 8° C., 9° C., 10° C., 11° C., 12° C., 13° C., 14° C., 15° C., 16° C., 17° C., 18° C., 19° C., 20° C., 21° C., 22° C., room temperature, 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. or 60° C.

The wording that the "bringing into contact of the biological sample with the composition" is carried out "at a temperature in a range of from −80° C. to +80° C." or at one of the other temperatures mentioned hereinabove means that the temperature of the mixture obtained after the bringing into contact of the biological sample with the composition is within the abovementioned temperatures. Thus, the biological material may take the form of a sample frozen at temperatures of below −20° C., for example a sample stored in liquid nitrogen, and in such a case an amount of composition, or a composition with a temperature, will be employed such that the temperature of the mixture (and thus also the temperature of the biological sample) obtained after the bringing into contact of the frozen biological sample with the composition is within the abovementioned temperature range.

In accordance with a particular embodiment of the method according to the invention, it may also be preferred that the biological sample after the bringing into contact with the composition in method step ii), preferably under the abovementioned temperature conditions, is additionally stored in a method step iii), which follows method step ii), at a temperature in a range of from −80° C. to +80° C., preferably in a range of from 0° C. to +80° C., even more preferably in a range of from 2, 3, 4, 5, 6, 7 or 8° C. up to +80° C. and more preferably in a range of from 18° C. to +80° C., for example at a temperature of at least −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., room temperature, 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. or 60° C., where such a storage may be effected over a period of at least one day, preferably at least 2 days, more preferably at least 3 days, optionally at least one week, at least two weeks, at least one month, at least three months, at least six months or else at least 12 months.

The method according to the present invention makes it possible to store a treated biological sample at room temperature, at refrigeration temperatures or at even higher temperatures without this resulting in a discernible degradation of biomolecules such as nucleic acids or proteins in the biological sample. This is a significant advantage over traditional stabilizing methods since the method can be carried out without the use of liquid nitrogen or of cooling devices and the stabilized sample can also be stored without the use of liquid nitrogen or of cooling devices.

After the treatment according to the invention, and if appropriate before or else after a possible storage step iii), the treated biological sample may also be embedded in suitable embedding means, for example in paraffin or the like, so that tissue sections which are suitable for histological studies can then be prepared in a simpler manner from the biological sample.

In accordance with a particular embodiment of the method according to the invention, it may furthermore be preferred additionally to follow method steps i) and ii) with a method step iv) histological analysis of the biological sample brought into contact with the composition, or analysis of biomolecules in, or from, the biological sample brought into contact with the composition, where this method step iv) can, if appropriate, also be carried out before or after storage in accordance with the above-described method step iii).

A histological study is preferably understood as meaning any study method which is suitable for analyzing the morphological state of a tissue, a tissue section, a cell or of subcellular structures, for example by means of microscopy and, if appropriate, using staining or labeling techniques known to the skilled worker.

Suitable biomolecules which can be analyzed are all those biomolecules which are known to the skilled worker, in particular natural, modified or synthetic nucleic acids, natural, modified or synthetic proteins or oligopeptides, hormones, growth factors, metabolic substrates, lipids, oligosaccharides or proteoglucans. Suitable nucleic acids are all those nucleic acids which are known to the skilled worker, in particular ribonucleic acids (RNAs), for example mRNA, siRNA, miRNA, snRNA, t-RNA, hnRNA or ribozymes, or deoxyribonucleic acids (DNAs). In principle, they may take the form of any type of polynucleotide which is an N-glycoside or C-glycoside of a purine or pyrimidine base. The nucleic acid may be single-stranded, double-stranded or multi-stranded, linear, branched or circular. It may correspond to a molecule which occurs in a cell, such as, for example, DNA or messenger RNA (mRNA) or it can be generated in vitro, such as complementary DNA (cDNA), antisense RNA (aRNA) or synthetic nucleic acids. The nucleic acid can consist of few subunits, at least two subunits, preferably eight or more subunits, such as, for example, oligonucleotides, several hundred of subunits up to several thousand of subunits such as, for example, certain expression vectors, or many more subunits, such as genomic DNA. Preferably, the nucleic acid comprises the coding information for a polypeptide in functional linkage with regulatory sequences which permit the expression of the polypeptide in the cell in (to) which the nucleic acid is introduced or is naturally present. Thus, a preferred embodiment of the nucleic acid is an expression vector. In another embodiment, it is a pDNA (plasmid DNA), an siRNA, an siRNA duplices or an siRNA heteroduplices, with the term "siRNA" being understood as meaning ribonucleic acids with a length of approximately 22 nucleotides which are generated by cleaving a double-stranded RNA (dsRNA) with the enzyme "dicer" and introduced into the enzyme complex "RISC" (RNA-induced silencing complex).

In this context, the wording "analysis of biomolecules in, or from, the biological sample brought into contact with the composition" means that the analysis may take place both in situ and ex situ, i.e. for example after isolation of the biomolecules from the biological sample. If biomolecules from a biological sample are to be isolated for analytical purposes, it may be advantageous, in particular in the case of cells, tissues or other complex or compact samples, first to homogenize the samples, which may be carried out via mechanical means, for example by means of cannulas, mortars, rotor-stator homogenizers, a ball mill and the like, via chemical means by using suitable lysis buffers, which usually comprise detergents and/or chaotropic substances, via enzymatic means, for example using proteases, or by a combination of these measures.

To carry out a histological analysis, or to carry out an analysis of biomolecules, in or from the biological sample, it is possible to employ all analytical methods which are known to the skilled worker and which he deems suitable, preferably methods selected from the group consisting of light microscopy, electron microscopy, confocal laser scanning microscopy, laser micro dissection, scanning electron microscopy, Western blotting, Southern blotting, enzyme-linked immunosorbent assay (ELISA), immune precipitation, affinity chromatography, mutation analysis, polyacrylamide gel electrophoresis (PAGE), in particular two-dimensional PAGE, HPLC, polymerase chain reaction (PCR), RFLP analysis (restriction fragment length polymorphism analysis), SAGE analysis (serial analysis of gene expression), FPLC analysis (fast protein liquid chromatography), mass spectrometry, for example MALDI-TOF mass spectrometry or SELDI mass spectrometry, microarray analysis, LiquiChip analysis, enzyme activity analysis, HLA typing, sequencing, WGA (whole genome amplification), RT-PCR, real-time PCR or real-time RT-PCR, RNase protection analysis or primer extension analysis.

In accordance with a particular embodiment of the method according to the invention, method step iv) comprises both a histological analysis of the biological sample and an analysis of biomolecules in or from the biological sample. In accordance with a further particular embodiment of the method according to the invention, method step iv) comprises both an analysis of nucleic acids in or from the biological sample and an analysis of proteins in or from the biological sample.

The biological sample treated by the method according to the invention also contributes to achieving the objects mentioned at the outset.

A first device for treating a biological sample, comprising, as components:

(β1) at least one vessel with at least one port for receiving a fluid up to a filling level h, (β2) at least one lid for sealing the at least one port, (β3) at least one immersion aid which is connected to at least one of the lids (β2), and (β4) a mixing device which is arranged rotatably about an axis L and which comprises guide vanes for mixing the fluid in the at least one vessel (β1)

also contributes to achieving the objects mentioned at the outset.

If the compositions according to the invention are employed for treating a biological sample, this may result in the problem that firstly it is difficult to immerse the sample in the composition and secondly that good mixing of the composition, which is advantageous in order to obtain inhomogeneities which occur after the sample has been immersed into the composition, in particular in the immediate environment of the biological sample, is made difficult, the reason being the high viscosity of the composition, which depends on the type and quantity of the polyol present in the composition.

These difficulties can be overcome by means of the first device according to the invention, since the immersion aid ($\beta 3$) makes possible the immersion of the biological sample in the composition and the mixing device ($\beta 4$) makes possible the mixing of the composition, and therefore homogeneous penetration of the sample by the composition.

The vessel ($\beta 1$) which is employed can take the form of any vessel which is known to the skilled worker and is suitable for this purpose. Vessels which are preferred in accordance with the invention are those vessels which are disclosed in U.S. Pat. No. 6,602,718 and in US 2004/0043505 A1 as the vessel with the reference number 12, in US 2005/0160701 A1 as the vessel with the reference number 14, in US 2003/0086830 A1 as the vessel with the reference number 152, in US 2003/0087423 A1 as the vessel with the reference number 12 or in WO 2005/014173 A1 as the vessel with the reference number 100. The disclosure of these publications regarding suitable vessels for receiving biological samples is herewith incorporated by reference and forms part of the disclosure of the present invention.

If a cylindrical vessel is employed as vessel ($\beta 1$), the diameter of vessel ($\beta 1$) is preferably in a range of from 5 to 500 mm, particularly preferably in a range of from 10 to 200 mm and most preferably in a range of from 10 to 30 mm.

The lid ($\beta 2$) which is employed can take the form of any lid which is known to the skilled worker and is suitable for this purpose. Lids which are preferred in accordance with the invention are those lids which are disclosed in U.S. Pat. No. 6,602,718 and in US 2004/0043505 A1 as the lid with the reference number 22, in US 2005/0160701 A1 as the lid with the reference number 40, in US 2003/0086830 A1 as the lid with the reference number 14, in US 2003/0087423 A1 as the lid with the reference number 14 or in WO 2005/014173 A1 as the lid with the reference number 22. The disclosure of these publications regarding suitable lid for sealing the vessels suitable for receiving biological samples is also incorporated by reference and forms part of the disclosure of the present invention.

In accordance with a particular embodiment of the first device according to the invention, the filling level h is 20 to 99%, particularly preferably 40 to 90% and most preferably 50 to 80% of the total height H of the vessel ($\beta 1$).

Besides the vessel ($\beta 1$) and the lid ($\beta 2$), the first device according to the invention also comprises an immersion aid ($\beta 3$).

This immersion aid ($\beta 3$) may, in principle, take the form of any device which is suitable for fully immersing, into the liquid, a sample which rests for example on the surface of a liquid present in the vessel ($\beta 1$) or which, if the immersion aid ($\beta 3$) comprises a receptacle for a biological sample, is located in or on the immersion aid ($\beta 3$), when the lid ($\beta 2$) is closed.

In the simplest case, the immersion aid ($\beta 3$) may take the form of a stamp whose cross-section corresponds approximately to the cross-section of the vessel ($\beta 1$).

Here, it is preferred that at least part of the immersion aid ($\beta 3$) is provided with openings through which upon closing the lid ($\beta 3$) the liquid present in the vessel ($\beta 1$) can escape so that closure of the lid does not result in compression of the fluid. Preferably, therefore, at least part of the immersion aid ($\beta 3$) is made of a mesh-like or sieve-like material. It is also feasible in the case of an immersion aid ($\beta 3$) which is not provided with openings for allowing the liquid to escape to apply projections underneath the immersion aid ($\beta 3$) which act as spacers between the immersion aid ($\beta 3$) and the sample so that the liquid and the sample are fully in contact, but in such a case the cross-section of the immersion aid ($\beta 3$) should be smaller than the cross-section of the vessel ($\beta 1$) in order to avoid compression of the fluid upon immersion of the immersion aid ($\beta 3$).

Besides a simple stamp, the immersion aid ($\beta 3$) may also be designed as a sample holder. Such an immersion aid is described for example in US 2003/0087423 as the sample holder with the reference number 152. The disclosure of US 2003/0087423 with regard to the structure and nature of the sample holder is herewith incorporated by reference and forms part of the disclosure of the present invention. In particular, this sample holder may be provided with a port through which a biological sample can be introduced into the interior of the sample holder, it being possible for this port to be sealed after the sample has been introduced. Again, it is preferred that the side panels or the bottom are made at least in part of a mesh-like or sieve-like material so that a fluid which is located in the vessel ($\beta 1$) can come into contact with the sample located in the sample holder upon closure of the lid ($\beta 2$). Moreover, the sample holder may also be designed as a simple clamp, for example, which is capable of clamping a biological sample, the clamp being fixed to the lid ($\beta 2$) in such a way that the clamped sample immerses into the fluid upon closure of the lid ($\beta 2$).

It is preferred in accordance with the invention that the immersion aid ($\beta 3$) penetrates the vessel ($\beta 1$) up to a height h', which reaches no more than to the filling level h, but particularly preferably no more than 80%, even more preferably no more than 50% of the filling level h in the sealed state of the vessel ($\beta 1$).

Furthermore, the first device according to the invention comprises a mixing device ($\beta 4$) arranged rotatably about an axis L and comprising guide vanes for mixing the fluid in the at least one vessel ($\beta 1$). Preferably, these guide vanes are arranged, designed and dimensioned in such a way in comparison with the diameter of the vessel ($\beta 1$) that upon uniformly turning the mixing device ($\beta 4$) about the axis L at a rotational speed of 10 rotations per minute a drop (2 μl) of a dye solution of 1 g potassium permanganate in one liter of water, which drop is introduced into the center of the vessel ($\beta 1$), gives, at room temperature, an apparently homogeneous distribution of the dye in all of the vessel ($\beta 1$) after one minute, preferably after 60 seconds, particularly preferably after 30 seconds, even more preferably after 15 seconds and most preferably after 10 seconds when the device is filled with water to 90% of the total height H of the vessel ($\beta 1$).

In the simplest case, this mixing device ($\beta 4$) can consist for example of a pin arranged above, below or at the level of the immersion aid, the length of which pin corresponds approximately to the diameter of the vessel ($\beta 1$) and whose center is connected to the center of the lid via a connection. When the lid ($\beta 2$) is screwed shut, the movement of the pin in the inside of the vessel ($\beta 1$) leads to mixing of the fluid.

In principle, the mixing device ($\beta 4$) may be connected to the lid ($\beta 2$) rigidly, preferably integrally, so that mixing only takes place when the lid ($\beta 2$) is turned, which is the case for example when the vessel ($\beta 1$) is sealed. It is also feasible to arrange the mixing device ($\beta 4$) so that it can be actuated for example by means of a wheel which is connected to the mixing device ($\beta 4$), or else by means of a lever which is connected to the mixing device (β4), the lever or wheel preferably being located outside the vessel (β1), particularly preferably underneath the bottom or above the lid (β2). In such a case, the mixing device (β4) can also be actuated when the lid (β2) is not being turned, which is advantageous in particular when a sterile environment is to be maintained within the device. It is furthermore possible to employ a suitable combination of a specific screw located on the vessel (β1) and a specific lid (β2), which combination is characterized in that the lid can be screwed onto the vessel via the screw and, once the lid has passed through all of the screw, can be rotated freely on the vessel. Such a closure is known for example on containers with toxic or corrosive substances as a child protection. While in this case the mixing device (β4) can also only be actuated when the lid is turned, turning of the lid does not necessarily result in the vessel (β1) being opened.

In accordance with a particular embodiment of the first device according to the invention, the immersion aid (β3) is a component of the mixing device (β4). In this case, the guide vanes for mixing the fluid are arranged on the immersion aid (β3) or form part of the immersion aid (β3).

In accordance with a particularly preferred embodiment of the first device according to the invention, the device is filled to at least 10%, particularly preferably to at least 20%, more preferably to at least 30%, even more preferably to at least 40% and most preferably to at least 50% of the total height H with the composition described in the context of the method according to the invention comprising at least one polyol and, if appropriate, one or more additives.

Furthermore, it may be preferred according to the invention that the first device according to the invention comprises a lid (β2) which is penetrated by a needle as described for example in WO 2005/014173 A1, it being especially preferred in this context that the vessel is filled with the composition described in the context of the method according to the invention, that a subatmospheric pressure prevails in the vessel and that the immersion aid is arranged in the vessel in such a way that it can be moved vertically along the height h even without the lid being open. In this manner, it is possible to draw up a defined amount of a fluid as the biological sample, for example a defined amount of blood, by subatmospheric pressure in the vessel (β1), through the lid into the vessel (β1), to inject this liquid sample into the composition comprising at least one polyol and, if appropriate, at least one additive by vertical motion of the immersion aid (β3) and then intimately to mix the liquid biological sample and the composition by means of the mixing device (β4).

A second device for treating a biological sample, comprising as components:

(β1) at least one vessel with at least one port for receiving a fluid up to a filling level h and having a cross-sectional area $A_{vessel}$, where the vessel is filled with the composition described in the context of the method according to the invention comprising at least one polyol and, if appropriate, at least one additive up to the filling level h, (β2) at least one lid for sealing the at least one port, and (β5) at least one body which has a cross-sectional area $A_{body}$, which is not connected to the vessel (β1) or the lid (β2), and which is located within the vessel, the ratio $A_{body}/A_{vessel}$ preferably being in a range of from approximately 0.02 to 0.95%, particularly preferably approximately 0.1 to 0.9% and most preferably approximately 0.2 to 0.5% further contributes to achieving the abovementioned aims.

Figure 5:
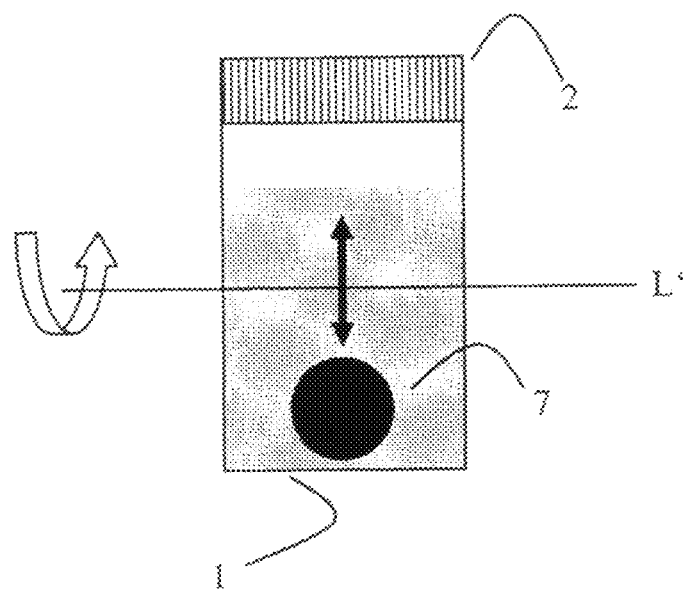
FIG. 5 shows a lateral view of an embodiment of the second device according to the invention.
Figure 5A:
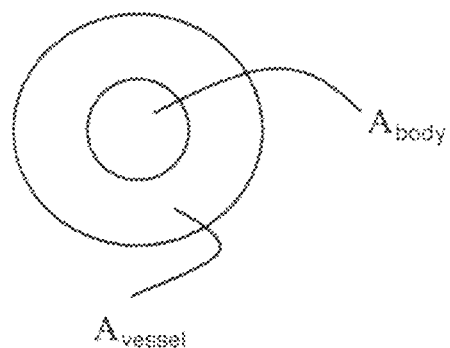
FIG. 5a shows a top view of the device with the body (β5) which is located therein.

The wording "not connected to the vessel (β1) or the lid (β2)" is taken to mean that the body (β5) can move freely within the vessel, in particular within the composition. When a biological sample, for example a small tissue fragment which, owing to the high viscosity of the composition first remains on the surface of the composition, is introduced into this second device according to the invention, sufficient immersion of the composition into the composition can be achieved with this device according to the invention also by tilting the device about the axis L', as shown in FIG. 5. This causes the body (β5) within the vessel (β1) to be moved perpendicularly to the cross-sectional area $A_{vessel}$, which, as the result of the flows thus generated along the moving body, leads to mixing of the composition.

Particularly preferred as vessel (β1) and as lid (β2) are those vessels and lids which have already been described at the outset in the context of the first device according to the invention.

In accordance with a particular embodiment of this second device according to the invention, the filling level h to which the device is filled with the composition amounts to 20 to 99%, particularly preferably 40 to 90% and most preferably 50 to 80% of the total height H of the vessel (β1).

In this context, the body (β5) can have any shape, but is preferably a sphere or cuboid, but particularly preferably a sphere. Moreover, it is also possible for a plurality of bodies (β5), for example for two, the, four or five, if appropriate also up to 10, 20 or 30 of such bodies, to be present in the vessel (β1).

It is furthermore preferred that the body is made of a material whose density exceeds the density of the composition by at least 5%, particularly preferably by at least 10%, more preferably by at least 20%, even more preferably by at least 50% and most preferably by at least 100%.

In accordance with a particularly preferred embodiment of this second device according to the invention, where the diameter of the vessel (β1) is in a range of from 5 to 500 mm, particularly preferably in a range of from 10 to 200 mm and most preferably in a range of from 10 to 30 mm, the body (β5) takes the form of a steel ball with a diameter in a range of from 1 to 20 mm, particularly preferably 5 to 10 mm. In principle, the body (β5) may also be magnetic, in which case the body (β5) may, for example, take the form of a stirring bar.

Furthermore, it may be preferred that the second device according to the invention comprises a lid (β2) which is penetrated by a needle as described for example in WO 2005/014173 A1, it being particularly preferred in this context too that a subatmospheric pressure prevails in the vessel. In this manner, it is possible to draw up a defined amount of a fluid as the biological sample, for example a defined amount of blood, by means of the subatmospheric pressure in the vessel (β1), through the lid into the vessel (β1) and to ensure homogeneous mixing of the biological sample and the composition by moving, preferably by tilting or turning the vessel (β1) about the axis L'.

In a particularly preferred embodiment, both the first and the second device according to the invention may be sterile, in particular in the interior of the vessel.

A kit comprising (γ1) the composition described in the context of the method according to the invention comprising the at least one polyol and, if appropriate, the at least one additive, and (γ2) one of the above-described devices or another vessel, preferably sealable vessel, which the skilled worker deems suitable for receiving this composition, for example a Greiner tube, a Falcon tube, an Eppendorf vessel or one of the vessels described in the publications U.S. Pat. No. 6,602,718, US 2004/0043505 A1, US 2005/0160701 A1, US 2003/0086830 A1, US 2003/0087423 A1 or WO 2005/014173 A1.

furthermore contributes to achieving the object mentioned at the outset.

In this context, the composition may already have been dispensed into the device or the vessel (γ2), as is for example also the case in the second device according to the invention. However, it is also feasible that the kit comprises, as further component, a dosing device (γ4), which is filled with the composition and by means of which defined portions of the composition can be filled into the device or the vessel (γ2), preferably under sterile conditions. Such a dosing device (γ4) may be designed for example in the form of a soap dispenser.

A kit comprising
(γ1) the composition described in the context of the method according to the invention comprising the at least one polyol and, if appropriate, the at least one additive, and
(γ3) reagents for analyzing biomolecules in or from a biological sample or for analyzing the morphology of a biological sample furthermore contributes to achieving the objects mentioned at the outset.

The reagents for analyzing biomolecules in or from a biological sample or for analyzing the morphology of a biological sample may, in principle, take the form of all reagents known to the skilled worker which can be used for or in the morphological analysis of a biological sample or for or in the analysis of biomolecules in or from a biological sample. These reagents comprise in particular dyes for staining cells or cell components, antibodies, optionally labeled with fluorescent dyes or with enzymes, an absorption matrix such as, for example, DEAE-cellulose or a silica membrane, substrates for enzymes, agarose gels, polyacrylamide gels, solvents such as ethanol or phenol, aqueous buffer solutions, RNase-free water, lysis reagents, alcoholic solutions and the like.

A kit comprising
(γ1) the composition described in the context of the method according to the invention comprising the at least one polyol and, if appropriate, the at least one additive,
(γ2) one of the above-described devices or another vessel, preferably sealable vessel, which the skilled worker deems suitable for receiving this composition, and
(γ3) reagents for analyzing biomolecules in or from a biological sample or for analyzing the morphology of a biological sample.

furthermore contributes to achieving the objects mentioned at the outset.

Again, the composition may also be dispensed in the device or the vessel (γ2) or else the kit may comprise a suitable dosing device (γ4).

The use of the above-described devices or of one of the above-described kits for treating a biological sample, the use of the devices according to the invention or of one of the above-described kits in the method according to the invention for treating a biological sample, and the use of a composition comprising at least one polyol and, if appropriate, at least one additive, as described in the context of the method according to the invention, for treating a biological sample, in particular for stabilizing a biological sample, also contribute to achieving the objects mentioned at the outset.

A method of treating a disease, comprising the method steps:
(σ1) diagnosis of the disease by a diagnostic method which comprises the analysis of a biological sample by means of the method according to the invention comprising method steps i), ii) and iv), and
(σ2) therapeutic treatment of the disease which has been diagnosed also contributes to achieving the objects mentioned at the outset.

The invention will now be illustrated in greater detail with the aid of nonlimiting figures and examples.

Figure 2:
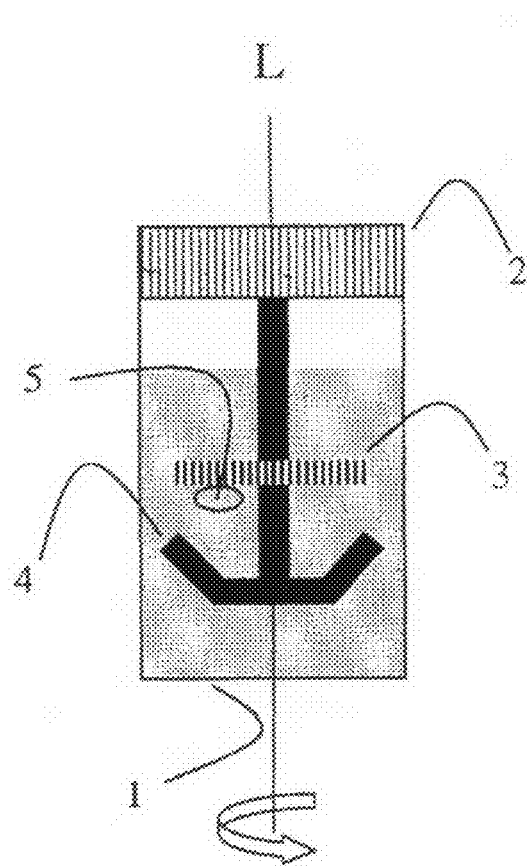
FIG. 2 shows a lateral view of a further embodiment of the first device according to the invention, where the mixing device (β4) is arranged below the immersion aid (β3).
Figure 3:
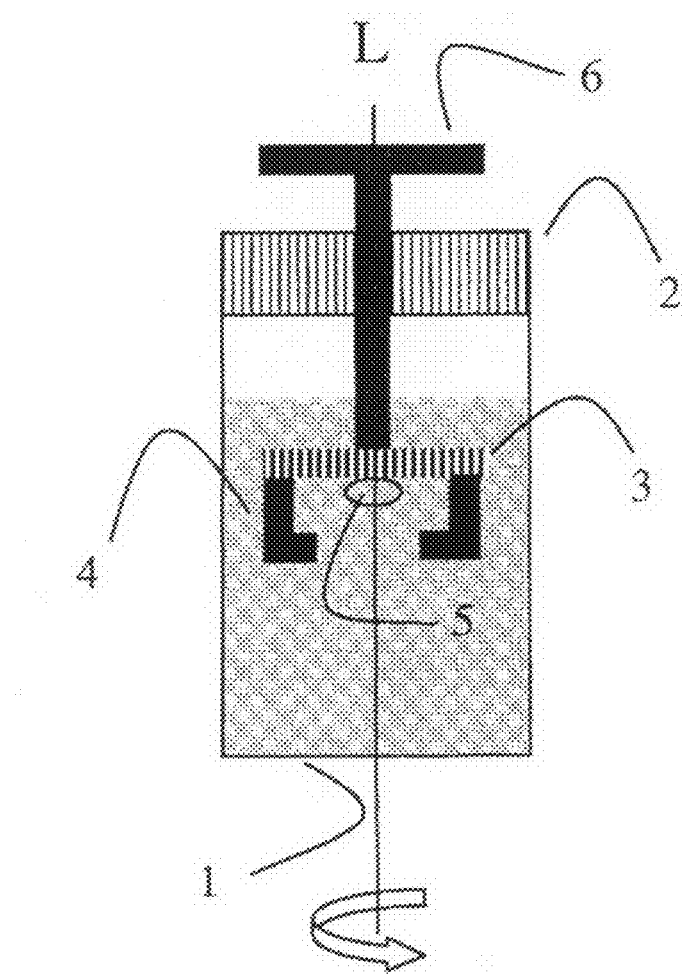
FIG. 3 shows a lateral view of a further embodiment of the first device according to the invention, where the mixing device (β4) is a component of the immersion aid (β3).

The device shown in FIG. 1 comprises a vessel 1 with a total height H, which can be sealed with a lid 2. The vessel 1 is filled up to the filling level h with a composition, preferably a liquid composition, preferably with the composition comprising the at least one polyol and, if appropriate, the at least one additive. An immersion aid 3, which is designed in the manner of a mesh or screen, is connected to the lid 2. Upon closing the lid 2, the sample 5, which before immersing the immersion aid 3, has been located on the surface of the composition, is immersed in the composition, during which method the immersion aid 3 penetrates the vessel 1 up to the level h' when the vessel 1 is closed. When the lid 2 is screwed shut, the guide vanes 4 of the mixing device which are arranged above the immersion aid 3 result in the composition being mixed. As can be seen from FIGS. 1a and 1b, the guide vanes 4 of the mixing device can be designed in different shapes. FIGS. 1a and 1b show four guide vanes 4, but in principle it is also possible to use less than four or more than four guide vanes 4 as long as rotating the mixing device about the axis L ensures sufficient mixing of the composition in the vessel 1. According to FIG. 2, the guide vanes 4 may also be arranged below the immersion aid 4, while, as shown in FIG. 3, the guide vanes 4 may also be a component of the immersion aid 3. In this case, the immersion aid 3 may have for example one or more projections which extend radially (that is to say perpendicularly to the axis L), which projections are designed for example in the shape of small blades. It is particularly preferred in accordance with the invention when, as shown in FIG. 3, the guide vanes 4 are as close as possible to the biological sample 5 since in such a case as thorough as possible a mixing of the composition in the immediate vicinity of the sample, and thus a particular homogeneous penetration of the sample 5 with the composition, can be ensured. The device shown in FIG. 3 furthermore also comprises a wheel 6 over which the guide vanes 4 of the mixing device can be moved even when the lid 2 is closed and is not moved.

FIG. 4 shows a device where the immersion aid 3 comprises a sample receptacle as is known from US 2003/0087423 A1. Here, the immersion aid 3, which is provided with a sample receptacle, can also be designed in such a way that it has oblique side panels (and thus has, when viewed from above, a trapezoid outline), so that these oblique side panels act as guide vanes 4 when the immersion aid is rotated about the axis L (see FIG. 4b).

FIG. 5 shows an embodiment of the second device according to the invention. This device is filled with the composition described at the outset up to the filling level h, a steel ball 7 being located in the interior of the vessel 1. When the device is tilted about the axis L', the steel ball moves in the direction of the arrow shown in FIG. 5, resulting in the mixing of the composition.

EXAMPLES

1. Histological Analysis of Samples Treated According to the Invention

Immediately after the removal of organs, rat liver tissue was treated with in each case 1 ml of the compositions detailed in table 1 and stored for 1 day in the incubator at 25°

C. After storage, the tissue pieces are removed from the solutions, transferred into plastic boxes and, following conventional protocols, incubated in an ascending ethanol series and in xylene, and embedded in paraffin. With the aid of a microtome, sections are prepared from the paraffin-embedded tissue, and these sections are stained on the slide with hematoxylin-eosin by customary methods. The stained tissue sections are viewed under the light microscope. The result is compiled in table 1:

TABLE 1

| Composition | Result |
| --- | --- |
| 1,2,3-Propanetriol | Morphology retained |
| 1,2,6-Hexanetriol | Morphology retained |
| 3-Methyl-1,3,5-pentanetriol | Morphology retained |
| 25% 1,2,3-propanetriol + 75% 1,2,6-hexanetriol | Morphology retained |
| 75% diethylene glycol + 25% 1,2,6-hexanetriol | Morphology retained |
| 75% 3-methyl-1,3,5-pentanetriol + 25% 1,2,3-propanetriol | Morphology retained |
| 75% 1,2,6-hexanetriol + 25% 3-methyl-1,3,5-pentanetriol | Morphology retained |
| 75% 1,2-propanediol + 25% 1,2,6-hexanetriol | Morphology retained |
| 50% triethylene glycol + 50% 1,2,6-hexanetriol | Morphology retained |
| 75% triethylene glycol + 25% 1,5-pentanediol | Morphology retained |
| 75% 1,2,6-hexanetriol + 25% 1,5-pentanediol | Morphology retained |
| 50% triethylene glycol + 50% 2,4-pentanediol | Morphology retained |
| 50% diethylene glycol + 50% 1,3-propanediol | Morphology retained |
| Diethylene glycol | Morphology retained |
| Triethylene glycol | Morphology retained |
| 1,3-Propanediol | Morphology retained |
| 25% DMSO + 75% 1,2,6-hexanetriol | Morphology retained |
| 50% DMSO + 50% 1,5-pentanediol | Morphology retained |
| 75% DMSO + 25% 2,4-pentanediol | Morphology retained |

As can be seen from table 1, the method according to the invention allows fresh tissue samples to be stabilized at room temperature conditions, it still being possible to carry out histological analyses with the samples thus stabilized.

1a. Histological Analysis of 1,2,3-propanetriol- and 3-methyl-1,3,5-pentanetriol-Treated Samples For this experiment, a composition composed of 25% of 1,2,3-propanetriol and 75% of 3-methyl-1,3,5-pentanetriol and a saturated, aqueous solution of paraformaldehyde (a cross-activating additive) are prepared. To prepare the final composition, 90% by volume of the triol mixture are mixed with 10% by volume of the paraformaldehyde solution.

Immediately after the removal of organs, rat liver and muscle tissue is treated with the final composition thus prepared and stored for 1 day at room temperature (18-25° C.). After storage, the tissue pieces are removed from the solutions, transferred into plastic boxes and, following conventional protocols, incubated in an ascending ethanol series and in xylene, and embedded in paraffin. With the aid of a microtome, sections are prepared from the paraffin-embedded tissue samples, and these sections are stained with hematoxylin-eosin by customary methods on the slide. The stained tissue sections are viewed under the light microscope.

It is shown clearly that the stabilizing solution fixes the tissue and that the tissue treated thus is suitable for histological studies.

2. RNA analysis of Stored Samples Treated According to the Invention

Immediately after the removal of organs, rat liver tissue was treated with in each case 1 ml of different solutions (see table 2) and stored at room temperature for up to 28 days and at 4-8° C. in the refrigerator for up to 3 months. After storage, the RNA is isolated from the stored samples.

To isolate RNA, the tissue is removed from the solutions after storage, and 350 µl of a commercially available guanidinium isothiocyanate buffer, such as, for example, RLT buffer from QIAGEN, Hilden, Germany, is added per 10 mg of tissue. The sample is homogenized with the aid of a ball mill, such as, for example, TissueLyzer from QIAGEN over a period of 2×2 min at 20 Hz using a 5 mm steel ball, during which method the guanidinium isothiocyanate buffer lyses the cells in the manner known from the prior art and denatures the proteins released. Thereafter, the lysates are centrifuged for 3 min at 14 000 rpm. 350 µl, which represents 10 mg of tissue, are removed from the supernatant. To these samples there is added 1 volume (350 µl) 70% ethanol, and the samples are mixed for a period of approximately 5 s by repeated pipetting up and down or by vortexing. Thereafter, the lysate is applied to a commercially available silica-membrane-containing spin column, such as, for example, RNeasy columns from QIAGEN, and passed across the membrane by centrifugation (1 min at 10 000×g). The RNA remains bound to the membrane and is subsequently washed with a first commercially available guanidinium-isothiocyanate-containing wash buffer, for example the buffer RW1 from QIAGEN. To enzymatically remove any total DNA which may be bound, DNaseI in a suitable buffer is subsequently applied to the column and incubated for 15 min at room temperature to degrade the bound DNA. Thereafter, the sample is washed again with a first commercially available guanidinium-isothiocyanate-containing wash buffer, for example the buffer RW1 from QIAGEN, and thereafter with a second Tris-containing or Tris- and alcohol-containing wash buffer, for example buffer RPE from QIAGEN. Here, the wash buffers are in each case passed across the membrane by means of centrifugation (1 min at 10 000×g). The wash step involving the second Tris-containing or Tris- and alcohol-containing wash buffer is repeated with a smaller volume, in which method the membrane is simultaneously dried by the centrifugation (2 min at maximum speed, in the present case 20 000×g). For the elution, 40 µl of RNase-free water are pipetted onto the membrane in order to detach the purified RNA from the membrane. After incubation for 1 min at a temperature in the range of from 10-30° C., the eluate is passed across the membrane by centrifugation (1 min at 10 000×g), and the elution step is repeated in order to make the elution complete.

The amount of total RNA which has been isolated is determined after dilution in water by photometrically measuring the light absorption at a wavelength of 260 nm. The quality of the RNA thus obtained is determined by photometrically determining the ratio of the light absorption at 260 nm to the light absorption at 280 nm. The results of the isolation steps are shown in table 2.

It can be seen from table 2 that it was possible to stabilize fresh biological samples at room temperature by means of the method according to the invention, and that sufficient amounts of RNA can still be isolated from these samples, even after storage periods of up to three months, the quality of this RNA being characterized by the ratio of the light absorption at 260 nm to the light absorption at 280 nm.

TABLE 2

| Composition | Storage temperature | Storage time | 260 nm/ 280 nm | Yield/ 10 mg tissue |
|---|---|---|---|---|
| 50% diethylene glycol + 50% 1,2,6-hexanetriol | 4° C. | 14 d | 1.9 | 48.9 |
| | | 28 d | 2.0 | 67.7 |
| | | 2 months | 1.9 | 54.4 |
| | | 3 months | 1.8 | 33.5 |
| 25% 1,3-propanediol + 75% 1,2,6-hexanetriol | 4° C. | 14 d | 1.9 | 57.5 |
| | | 28 d | 1.9 | 56.3 |
| | | 2 months | 1.9 | 51.5 |
| | | 3 months | 1.9 | 37.3 |
| 75% 1,2,3-propanetriol + 25% 1,2,6-hexanetriol | 4° C. | 14 d | 2.0 | 91.7 |
| | | 28 d | 2.0 | 82.8 |
| | | 2 months | 1.9 | 86.9 |
| | | 3 months | 1.9 | 40.0 |
| 75% 1,2,6-hexanetriol + 25% 1,5-pentanediol | 4° C. | 14 d | 2.0 | 80.8 |
| | | 28 d | 1.9 | 50.1 |
| | | 2 months | 1.9 | 90.7 |
| | | 3 months | 1.9 | 68.1 |
| 75% 1,2,6-hexanetriol + 25% 3-methyl-1,3,5-pentanetriol | 25° C. | 9 d | 2.0 | 46.3 |
| | | 14 d | 2.1 | 50.4 |
| | | 21 d | 2.1 | 57.3 |
| | | 28 d | 2.0 | 38.5 |
| 25% 1,2,3-propanetriol + 75% 3-methyl-1,3,5-pentanetriol | 25° C. | 9 d | 2.0 | 33.6 |
| | | 14 d | 2.0 | 42.8 |
| | | 21 d | 2.0 | 33.2 |
| | | 28 d | 2.0 | 41.8 |
| 3-Methyl-1,3,5-pentanetrol | 25° C. | 9 d | 2.1 | 47.0 |
| | | 14 d | 2.0 | 37.9 |
| | | 21 d | 2.0 | 47.9 |
| | | 28 d | 2.1 | 39.2 |
| 25% 1,2,3-propanetriol + 75% 1,2,6-hexanetriol | 25° C. | 9 d | 2.0 | 42.8 |
| | | 14 d | 2.1 | 58.4 |
| | | 21 d | 2.0 | 49.1 |
| | | 28 d | 2.1 | 37.3 |
| 25% 1,3-propanediol + 75% 1,2,6-hexanetriol | 25° C. | 10 d | 2.0 | 33.9 |
| | | 14 d | 1.9 | 30.8 |
| | | 21 d | 2.0 | 27.4 |
| | | 28 d | 1.9 | 43.5 |

2a. RNA Analysis of Samples Treated in Accordance with the Invention

To study the RNA-stabilizing properties of compositions comprising additives, compositions comprising different amounts of paraformaldehyde are prepared as described in example 1a (see table 2a). Immediately after the removal of organs, rat liver tissue is treated with in each case 1.5 ml of the final compositions and stored for 3 days at room temperature. Thereafter, the RNA is isolated in accordance with the method described in example 2. In each case three samples are studied.

Figure 8:
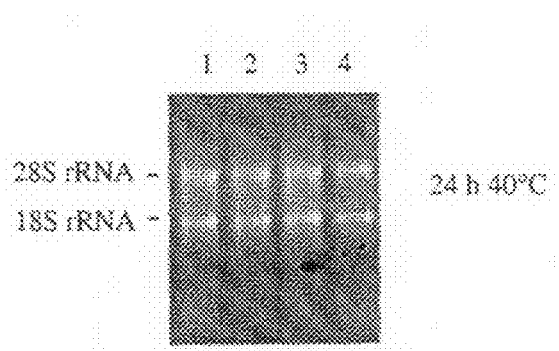
FIGS. 8, 8a and 8b show the results of the RNA analysis obtained in example 6 in the form of an agarose-formaldehyde-MOPS gel after the samples have been stored at high temperatures.
Figure 8A:
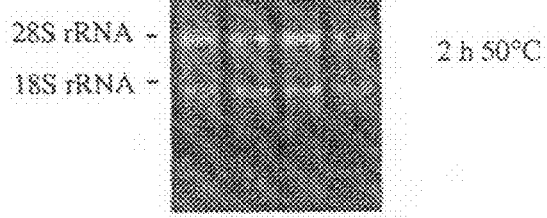

The amount of total RNA isolated is determined after dilution with water by photometrically measuring the light absorption at a wavelength of 260 nm. The quality of the RNA thus obtained is determined by photometrically determining the ratio of the light absorption at 260 nm to the light absorption at 280 nm. The results of the isolation steps are shown in table 2a. The means of the three samples studied are given in each case. In addition, the isolated RNA is analyzed on an agarose gel stained with ethidium bromide. To this end, for example 10 μl of the eluates are separated in a 1% formaldehyde agarose-MOPS gel. The result is shown in FIG. 8c.

TABLE 2a

| No. | Composition: Amount in % by vol. of a mixture of 25% 1,2,3-propanetriol and 75% 3-methyl-1,3,5-pentanetriol | Amount in % by vol. of a saturated paraformaldehyde solution | OD260/280 | RNA yield/μg |
|---|---|---|---|---|
| 1 | 99% by vol. | 1% by vol. | 2.3 | 48.3 |
| 2 | 96% by vol. | 4% by vol. | 2.2 | 31.3 |
| 3 | 90% by vol. | 10% by vol. | 2.3 | 45.8 |

The results show that the composition according to the invention, despite the admixture of a crosslinking additive (paraformaldehyde), surprisingly make possible the isolation of RNA in a very good quality and yield. The method according to the invention thus makes it possible not only to maintain the morphology of the sample, but also to stabilize the molecular constituents, such as nucleic acids.

2b. RNA Analysis after Long-term Storage of Samples Treated in Accordance with the Invention Immediately after the removal of organs, rat liver tissue is treated with 1 ml of a composition a) 25% of 3-methyl-1,2, 5-penantriol and 75% of 1,2,6-hexanetriol and stored at 4-8°

C. in the refrigerator for up to 12 months. Equally, rat kidney tissue is treated with 1 ml of composition b) 25% of 1,2,3-propanetriol and 75% of 3-methyl-1,2,5-penantriol and stored.

TABLE 2b

| No. | Storage time |
|---|---|
| 1 | 7 days |
| 2 | 14 days |
| 3 | 21 days |
| 4 | 28 days |
| 5 | 2 months |
| 6 | 3 months |
| 7 | 4 months |
| 8 | 5 months |
| 9 | 6 months |
| 10 | 9 months |
| 11 | 12 months |

At the points in time detailed in table 2b, the RNA is isolated from the samples stored in compositions a) and b), using the method given in example 2.

The RNA which has been isolated is analyzed on agarose gels stained with ethidium bromide. To this end, for example 1.0% formaldehyde agarose-MOPS gels are prepared. The result of the sample with composition a) is shown in FIG. 9a, and the result of the sample with composition b) is shown in FIG. 9b.

Both figures show clearly that the method according to the invention preserves the RNA without freezing, even over very long periods.

3. DNA Analysis of Stored Samples Treated in Accordance with the Invention

Immediately after the removal of organs, rat lung tissue was treated with in each case 1 ml of different solutions (see table 3) and stored for 6 days at 25° C. After the storage, the DNA is isolated from the stored samples.

To isolate the DNA, the tissue is removed from the solutions after storage, and per 10 mg of tissue in 180 µl of the buffer ALT from QIAGEN added. The sample is homogenized with the aid of a ball mill such as, for example, TissueLyzer from QIAGEN, over a period of 45 s at 25 Hz, using a 5 m steel ball. After 40µl of a Protease K solution (from QIAGEN) have been added, the lysates are incubated for 1 hour at 55° C., with shaking. After incubation, 220 µl of a commercially available guanidinium-hydrochloride-containing lysis buffer, such as the buffer AL from QIAGEN, are added, and the samples are mixed by vortexing. After mixing with 220 µl of 100% ethanol, the samples are applied to a silica-membrane-containing column (QIAamp Mini Spin Column from QIAGEN), and the lysate is passed across the membrane by means of centrifugation for 1 min at 10 000 rpm. The DNA remains bound to the membrane and is washed first with a first commercially available guanidinium-hydrochloride-containing wash buffer, for example with the buffer AW1 from QIAGEN, and thereafter with a second alcohol-containing wash buffer, for example buffer AW2 from QIAGEN. In this method, each of the wash buffers is passed across the membrane by centrifugation (1 min at 10 000×g or 3 min at 14 000×g). The DNA is eluted by applying 60 µl of the AE elution buffer (QIAGEN). After incubation for one minute, the elution buffer is passed across the membrane by centrifugation (1 min at 10 000×g) and the elution is repeated.

The amount of total DNA which has been isolated is determined after dilution in water by photometrically measuring the light absorption at a wavelength of 260 nm. The quality of the RNA thus obtained is determined by photometrically determining the ratio of the light absorption at 260 nm to the light absorption at 280 nm. The results of the isolation steps are shown in table 3.

TABLE 3

| Reagent | 260 nm/ 280 nm | Yield |
|---|---|---|
| 1,2,6-Hexanetriol | 1.9 | 30.9 |
| 3-Methyl-1,3,5-pentanetriol | 1.9 | 21.1 |
| 25% 1,2,3-propanetriol/75% 1,2,6-hexanetriol | 1.9 | 24.6 |
| 75% 1,2,3-propanetriol/25% 3-methyl-1,3,5-pentanetriol | 1.9 | 21.7 |
| 25% 1,2,3-propanetriol/75% 3-methyl-1,3,5-pentanetriol | 2.0 | 26.9 |
| 75% 1,2,6-hexanetriol/25% 3-methyl-1,3,5-pentanetriol | 1.9 | 14.7 |
| 50% 1,2,6-hexanetriol/50% 3-methyl-1,3,5-pentanetriol | 1.9 | 19.4 |

It can be seen from table 3 that the stabilization method according to the invention also makes it possible to isolate DNA in the stabilized samples in good quality and good yield, even after storage for six days at room temperature, and that, accordingly, the stabilization method according to the invention is suitable both for stabilizing RNA (see example 2) and for stabilizing DNA.

4. Protein Analysis of Stored Samples which have Been Treated According to the Invention Immediately after the removal of organs, rat liver tissue was treated with in each case 1 ml of different triols (see table 4) and was stored for 2 days and 7 days at 25° C. in the incubator. After the storage, a protein extract from the stored samples is prepared. Liver tissue which after its removal from the rat has been frozen directly in liquid nitrogen and subsequently stored at −80° C. is used as the control.

To prepare the protein extract, the tissue is removed from the stabilization composition after storage, and 400 µl of a customary extraction buffer, in the present case in a composition of 8M urea, 100 mM sodium dihydrogen phosphate and 10 mM Tris, pH 8.0, are added per 10 mg of tissue, and the sample is homogenized with the aid of a ball mill, for example the TissueLyzer from QIAGEN. The resulting lysate is centrifuged for 15 s at the highest possible speed (for example approx. 20 000×g) in order to pellet undissolved constituents. The proteinaceous supernatant is removed, and the protein concentration is determined by means of a Bradford assay. In each case 3 µg of protein are separated on an SDS-polyacrylamide gel by customary method, and the proteins in the gel are stained by means of Coomassie staining (see FIG. 6). The pattern of the stained protein bands is not altered during storage in comparison with the control. The proteins remain stable and are not subject to any degradation.

A second SDS-polyacrylamide gel with identical sample application is blotted onto a nitrocellulose membrane in a semidry blotting apparatus, following the manufacturer's instructions. The membrane is saturated with milk powder according to the prior art, hybridized with an ERK2-specific antibody, for example the Taq100 antibody from QIAGEN, following the manufacturer's instructions, and an immuno-detection is carried out. The results are also shown in FIG. 6.

Figure 6:
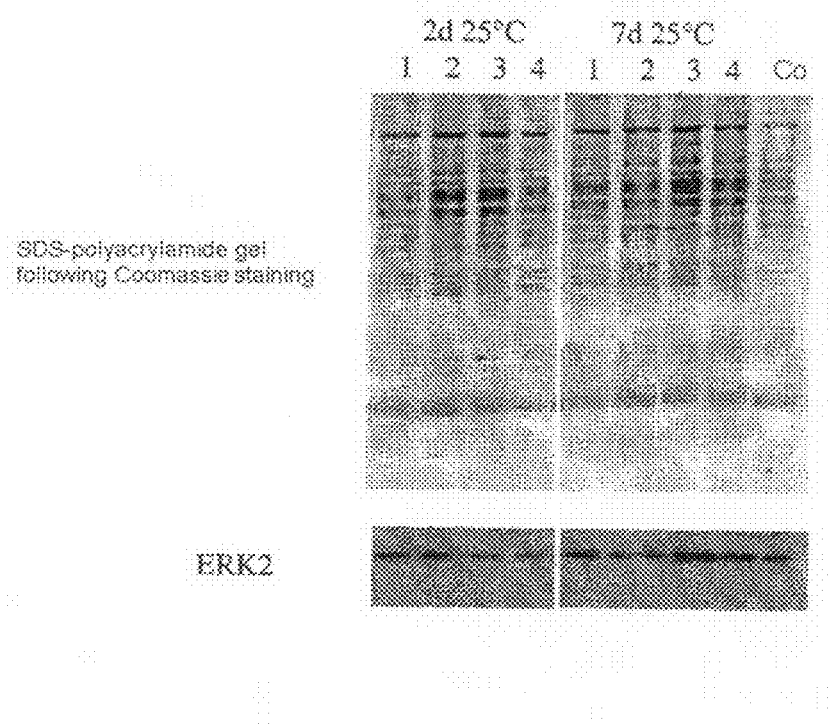
FIG. 6 shows the SDS polyacrylamide gel obtained in example 4 and the Western blot obtained in example 4.

It can be seen from FIG. 6 that proteins in the treated samples also remain intact as before and are not degraded, even after seven days' storage at room temperature, and can be isolated in good yield. Accordingly, the stabilization method according to the invention is suitable both for stabilizing nucleic acids (see examples 2 and 3) and for stabilizing proteins.

TABLE 4

| Lane | Composition |
|---|---|
| 1 | 1,2,4-Butanetriol |
| 2 | 3-Methyl-1,3,5-pentanetriol |
| 3 | 75% 1,2,3-propanetriol + 25% 1,2,6-hexanetriol |
| 4 | 1,2,6-Hexanetriol |
| Co | Control |

5. Protein Analysis of Stored Samples which Have Been Treated According to the Invention Immediately after the removal of organs, rat liver tissue is treated with in each case 1 ml of different triols (see table 5) and is stored for 2 days at 4-8° C. in the refrigerator. Tissue which immediately after the removal of organs has been frozen in liquid nitrogen and was stored frozen at −80° C. acts as the positive control.

After storage, the tissue is removed from the stabilization solutions, and 400 µl of an extraction buffer, described in the "LiquiChip Broad-Range Ser/Thr-Kinase" handbook from QIAGEN added per 10 mg of tissue. The samples are homogenized with the aid of a ball mill, for example TissueLyzer from QIAGEN, over a period of 5 min at 30 Hz, using a 5 mm steel ball and subsequently centrifuged in a bench top centrifuge over a period of 3 min at 14 000 rpm. The supernatant is removed and diluted 1:10 with the extraction buffer. The samples thus obtained are assayed for the activity of kinases, with the "LiquiChip Broad-Range Ser/Thr-Kinase" kit with the corresponding apparatus (LiquiChip Reader) from QIAGEN being employed, following the manufacturer's instructions. The manufacturer's assay buffer 1 without addition of protein is used as the negative control. Each sample is prepared and measured in duplicate.

Figure 7:
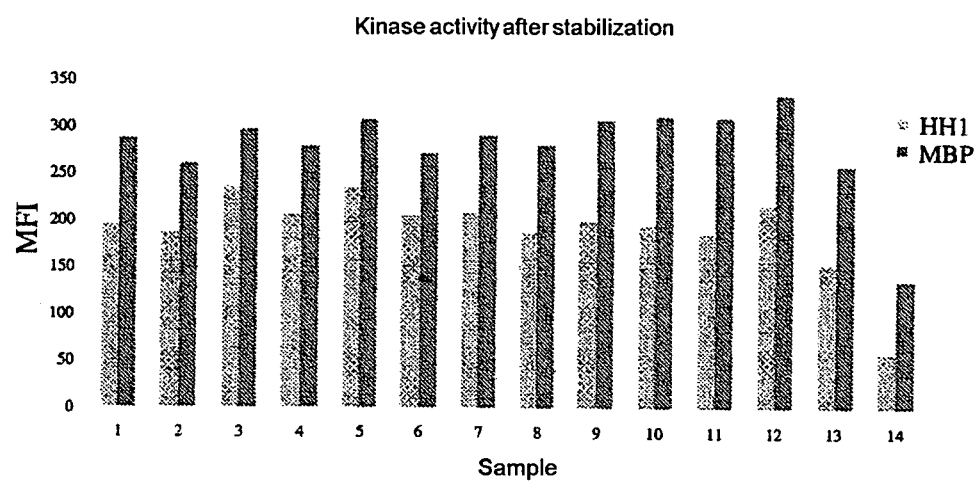
FIG. 7 shows the results of the enzyme activity analysis obtained in example 5 in the form of a bar diagram.

The results in the form of the mean of the fluorescence measured (MFI =medium fluorescence intensity) with the respective kinase substrate (HH: histone H1, MBP: myelin basic protein) are shown in FIG. 7.

The results show clearly that, following the treatment according to the invention and storage of the biological sample in accordance with the method according to the invention, the proteins isolated therefrom are again capable of displaying their activity. The stabilizing reagents are therefore also suitable for downstream analyses, which rely on native and active proteins.

TABLE 5

| Sample | Composition |
|---|---|
| 1 | 1,2,3-Propanetriol |
| 2 | 1,2,6-Hexanetriol |
| 3 | 3-Methyl-1,3,5-pentanetriol |
| 4 | 75% 1,2,3-propanetriol + 25% 1,2,6-hexanetriol |
| 5 | 50% 1,2,3-propanetriol + 50% 1,2,6-hexanetriol |
| 6 | 25% 1,2,3-propanetriol + 75% 1,2,6-hexanetriol |
| 7 | 75% 1,2,3-propanetriol + 25% 3-methyl-1,3,5-pentanetriol |
| 8 | 50% 1,2,3-propanetriol + 50% 3-methyl-1,3,5-pentanetriol |
| 9 | 25% 1,2,3-propanetriol + 75% 3-methyl-1,3,5-pentanetriol |
| 10 | 75% 1,2,6-hexanetriol + 25% 3-methyl-1,3,5-pentanetriol |
| 11 | 50% 1,2,6-hexanetriol + 50% 3-methyl-1,3,5-pentanetriol |
| 12 | 25% 1,2,6-hexanetriol + 75% 3-methyl-1,3,5-pentanetriol |
| 13 | Frozen (in liquid nitrogen) |
| 14 | Negative control |

5a. Protein Analysis after Long-term Storage of Samples Treated in Accordance with the Invention Immediately after the removal of organs, rat liver tissue is treated with in each case 1.5 ml of a composition of 25% of 3-methyl-1,2,5-penantriol and 75% of 1,2,6-hexanetriol and stored up to 6 months at 25° C. in the incubator or at 2-8° C. in the refrigerator. A protein extract is prepared from the stored samples at the points in time stated in table 5a.

TABLE 5a)

| No. | Storage time |
|---|---|
| 1 | 7 days |
| 2 | 14 days |
| 3 | 21 days |
| 4 | 28 days |
| 5 | 2 months |
| 6 | 3 months |
| 7 | 4 months |
| 8 | 5 months |
| 9 | 6 months |

To prepare the protein extract, the tissue is removed from the stabilization composition after storage, and 400 µl of a customary extraction buffer, in this case the mammalian lysis buffer from QIAGEN is added per 10 mg of tissue, and the sample is homogenized with the aid of a ball mill, for example the TissueLyzer from QIAGEN. The resulting lysate is centrifuged for 15 s at the highest possible speed (for example approx. 20 000×g) in order to pellet undissolved constituents. The proteinaceous supernatant is removed and the protein concentration is determined by means of a BCA assay, for example from Pierce.

In each case 3 µg of protein are separated on an SDS-polyacrylamide gel by customary methods and blotted onto a nitrocellulose membrane in a semidry blotting apparatus, following the manufacturer's instructions. The membrane is saturated with milk powder according to the prior art, hybridized with an actin-specific antibody and an ERK2-specific antibody, for example the Taq100 antibody from QIAGEN, following the manufacturer's instructions, and an immunodetection is carried out. The results with the ERK2-specific antibody are shown in FIG. 9c and the results with the actin-specific antibody are shown in FIG. 9c.

Figure 9:
FIG. 9 shows the results of the RNA analysis obtained in example 7 in the form of an agarose-formaldehyde-MOPS gel after the samples have been stabilized in penatols or hexaols.
Figure 9A:
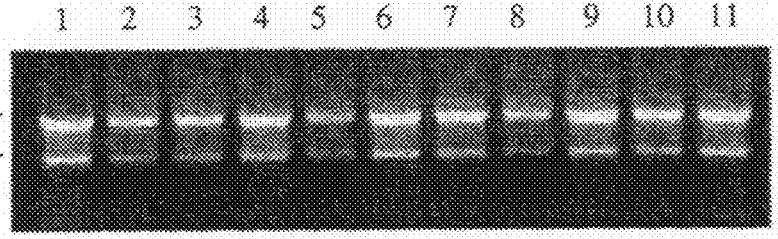
FIGS. 9a and 9b show the results of the RNA analyses obtained in example 2b in the form of an agarose-formaldehyde-MOPS gel.
Figure 9B:
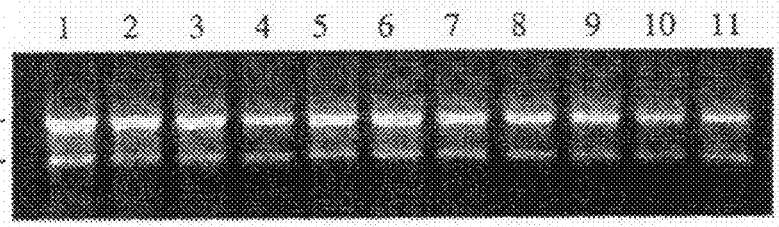
Figure 9C:
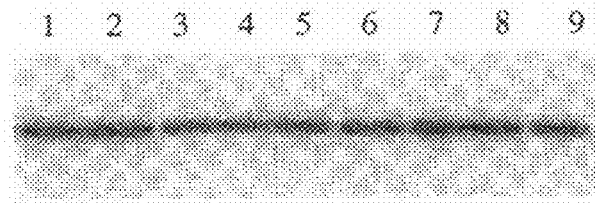
FIGS. 9c and 9d show the results of the protein analyses obtained in example 5a by means of BCA assays.
Figure 9D:
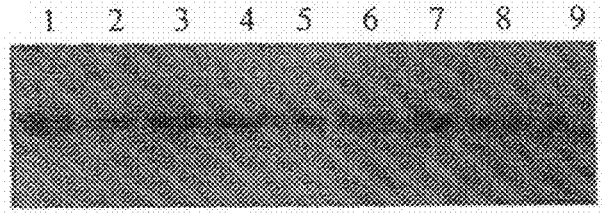

It can be seen from FIGS. 9c and 9d that it is also possible to preserve proteins in the stabilized samples over prolonged periods without freezing and even at high temperatures such as room temperature.

5b. Protein Analysis by Means of ELISA-technique of Samples which have Been Treated in Accordance with the Invention Immediately after the removal of organs, rat kidney tissue is treated with in each case 1.5 ml of a composition of 25% of 3-methyl-1,2,5-penantriol and 75% of 1,2,6-hexanetriol and stored for 7 days in the incubator at 25° C. Tissue samples which after the removal of organs are frozen immediately in liquid nitrogen and stored at −80° C. serve as the control. After storage, a protein extract is prepared.

To prepare the protein extract, the tissue is removed from the stabilization composition after storage, and 200 µl of a customary extraction buffer, in this case the mammalian lysis buffer from QIAGEN is added per 10 mg of tissue, and the sample is homogenized with the aid of a ball mill, for example the TissueLyzer from QIAGEN. The resulting lysate is centrifuged for 15 s at the highest possible speed (for example approx. 20 000×g) in order to pellet undissolved constituents. The proteinaceous supernatant is removed and the protein concentration is determined by means of a BCA assay, for example from Pierce. The lysate is standardized to a concentration of 2.5 mg/ml, and 20 µl of this dilute lysate are employed for the analysis. The analysis is carried out by means of the "LiquiChip Cell Signaling Detection Kits" for GAPDH and TBP together with the matching "Core Kit" on the corresponding workstation (Liquichip Workstation), following the manufacturer's (QIAGEN) instructions.

A pure buffer sample without tissue is employed for determining the background. The background is deducted from the sample data. Each sample is prepared and measured in triplicate.

The results are compiled in the form of the mean of the fluorescence measured (MFI=medium fluorescence intensity) for each of the proteins detected (GAPDH, TBP) in table 5b.

TABLE 5b

|  | GAPDH | TBP |
| --- | --- | --- |
| Control N2 | 1274 | 103 |
| 7 d 25° C. | 1446 | 100 |

The results demonstrate clearly that, after stabilization and storage of the biological sample in accordance with the method according to the invention, protein analyses of these samples are also possible by means of ELISA-based methods. Comparable protein quantities as in the control can be detected even after seven days' storage at 25° C.

6. RNA Analysis of Samples which have Been Treated in Accordance with the Invention and Stored at High Temperatures Immediately after the removal of organs, rat kidney tissue was treated with in each case 1 ml of 1,2,4-butanetriol (1), 3-methyl-1,3,5-pentanetriol (2), 1,2,6-hexanetriol (3) and a mixture of 75% of 1,2,3-propanetriol and 25% of 1,2,6-hexanetriol (4), and stored for 1 day at 40° C. or for 2 h at 50° C. in the incubator.

Alternatively, rat lung tissue is treated, after the removal of organs, with in each case 1 ml of 1,2,4-butanetriol (1) or 3-methyl-1,3,5-pentanetriol (2) and stored for 1 day at 4°-8° C. in the refrigerator. After a portion of the samples has been removed in order to isolate RNA (a), the tissue samples are stored for 1 h at 40° C. in the solutions. Thereafter, another portion of the samples is removed (b) and used for the isolation RNA. Thereafter, the remaining tissue samples in the solutions are again stored alternately for 1 h at 4-8° C. in the refrigerator and for 1 h at 40° C. in the incubator. After 4 cycles, the remaining after the last incubation at 40° C. are used for isolating RNA (c).

After the storage, the RNA from the stored samples is isolated as described in example 2.

The RNA which has been isolated is analyzed on agarose gels which have been stained with ethidium bromide. To this end, for example 1.0% formaldehyde agarose-MOPS gels are prepared. The result of the storage at 40° C. is shown in FIG. 8 and the result of the storage at 50° C. is shown in FIG. 8a. The result of the alternating storage at between 4° C. and 40° C. is shown in FIG. 8b.

Figure 8B:
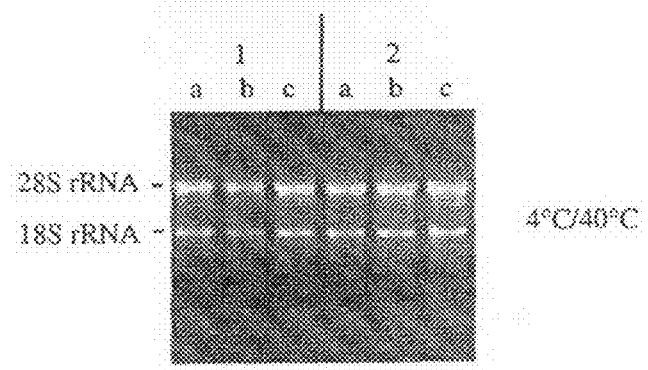
Figure 8C:
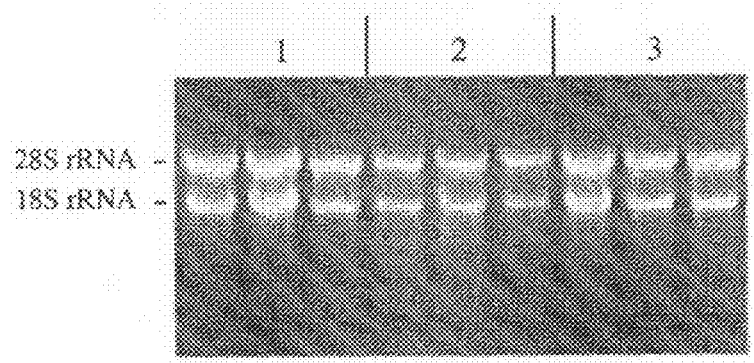
FIG. 8c shows the results of the RNA analysis obtained in example 2a in the form of an agarose-formaldehyde-MOPS gel.

It can be seen from FIGS. 8, 8a and 8b that sufficient amounts of intact RNA can be isolated from the samples stabilized in accordance with the invention even after storage at temperatures of 40° C. or 50° C.

7. RNA Analysis of Samples which have Been Treated in Accordance with the Invention Using Different Polyols Immediately after the removal of organs, rat spleen tissue was treated with in each case 1 ml of 1,2,3,4,5-pentanepentol (saturated solution in water)(1), 1,2,3,4,5,6-hexanehexaol (4.72M in water) (2) or 1,2,3-propanetriol (3) and stored for 1 day at 25° C. in the incubator (a) or for 3 days at 4-8° C. in the refrigerator (b).

After the storage, the RNA is isolated from the stored samples as described in example 2.

The RNA which has been isolated is analyzed on agarose gels which have been stained with ethidium bromide. To this end, for example 1.0% formaldehyde agarose-MOPS gels are prepared. The result is shown in FIG. 9.

It can be seen from FIG. 9 that the stabilization of biological samples can also be effected using pentaols or hexaols.

8. Treatment of Isolated Proteins in Accordance with the Method According to the Invention A purified reverse transcriptase, the enzyme "Omniscript" from QIAGEN was used to prove that the stabilizing reagents are suitable for stabilizing isolated proteins.

In each case 5 µg of the purified enzyme are treated with a 10 fold volume of the stabilizing reagents given in table 6. The mixtures are stored overnight at 4-8° C. in the refrigerator. To recover the enzyme from the stabilizing reagents, an automated purification based on nickel-NTA-affinity binding is carried out on the "Biosprint" apparatus, following the instructions of the manufacturer QIAGEN. Before the purification, all samples are made up to a total volume of 1 ml with the manufacturer's assay buffer, and in each case 50 µg of magnetic bead suspension was used. The controls used were firstly 5 µg of Omniscript in the manufacturer's storage buffer, which was stored under identical conditions (sample 6), and secondly 5 µg of Omniscript without previous storage in a stabilizing solution, which was simply subjected to the purification method (sample 7). Furthermore, 1 µl of the reverse transcriptase used for the experiment is used directly as positive control in the PCR, that is to say without storage and/or purification (sample 8).

TABLE 6

| Sample | Composition | Protein concentration [ng/ml] |
| --- | --- | --- |
| 1 | 1,2,6-Hexanetriol | 74 |
| 2 | 3-Methyl-1,3,5-pentanetriol | 62 |
| 3 | 75% 1,2,6-hexanetriol + 25% 3-methyl-1,3,5-pentanetriol | 52 |
| 4 | 50% 1,2,6-hexanetriol + 50% 3-methyl-1,3,5-pentanetriol | 58 |
| 5 | 25% 1,2,6-hexanetriol + 75% 3-methyl-1,3,5-pentanetriol | 50 |
| 6 | Storage in the manufacturer's storage buffer | 36 |
| 7 | No storage, purification | 54 |
| 8 | No storage, no purification | nd |
| 9 | No enzyme | nd |

The purified enzyme is used for checking the enzyme activity for a reverse transcription with subsequent PCR. To this end, the protein concentration after purification is measured by means of a customary Bradford reaction (results see table 6), and the purified enzyme is dialyzed with DTT (from QIAGEN) against the RT storage buffer. In each case 2 µl of the dialyzed protein fraction are employed for the reverse transcription. To carry out the reverse transcription, a reaction mixture for all reactions is prepared, consisting of 2 µl of a 10-fold concentrated reverse transcriptase buffer, 10 mM dNTP mix, 2 µM oligo-dT15 (Omniscript kit from QIAGEN), 75 ng of total RNA from Hela cells per reaction, and made up to a total volume of 18 µl per reaction with distilled water. This mixture is divided between the reaction vessels and in each case 2 µl of the respective Omniscript fraction are added. The reverse transcription proceeds over 1 h at 37° C. Water is added instead of the reverse transcriptase to act as the negative control (sample 9).

A 1.6 kb fragment of the human β-actin transcript is amplified in the PCR which follows. To this end, a reaction mixture for all reactions is prepared consisting of 2 µl of a 10-fold concentrated of the PCR buffer, 4 mM dNTP mix, 0.4 µl of a 25 mM magnesium chloride solution, in each case 0.8 ml of the primers, 4 µl of 5-fold concentrated Q solution and 0.25 ml of the Taq-DNA polymerase (PCR kit from QIAGEN), made up to a total volume of 19 µl per reaction with distilled water. The reaction mixture is divided between the reaction vessels, and in each case 1 µl of the previously generated cDNA is added. The no-template control used is water instead of the cDNA (NTC sample). The amplification proceeds as follows: 5 min at 93° C., 30 cycles of in each case 30 s at 93° C., 30 s at 55° C. and 90 s at 72° C., followed by one cycle of 5 min at 72° C. Each reaction is set up in duplicate.

After the amplification, in each case 10 µl of the PCR reactions are applied to 1% agarose-TAE gel and separated for 1 h at 120 V. The size marker used is the "Low DNA Mass Ladder" from Invitrogen. The results are shown in FIGS. 10 and 10a.

It can be seen from FIG. 10 that the method according to the invention is also suitable for storing and repurifying isolated proteins without the proteins being significantly affected in their activity.

9. RNA Analysis of Samples which have Been Treated in Accordance with the Invention Immediately after the removal of organs, rat spleen tissue was treated in each case with 1 ml of the compositions shown in table 7 and stored for 7 days at 25° C. Thereafter, the RNA is isolated from these samples in accordance with the method described in example 2.

The behavior of the RNA isolated thus is determined in a downstream analysis by PCR analysis. An RNA isolated from spleen tissue and frozen at −80 C was used as the control.

To determine the behavior of the isolated RNA, in each case 10 ng of total RNA in a total volume of 25 µl with a suitable mastermix for real-time RT-PCR, for example the Quantitect Probe RT-PCR kit from QIAGEN, and primer and sample of commercially available assays, for example from ABI, are employed in accordance with the manufacturer's instructions. The amplification is carried out in a suitable real-time amplification apparatus, for example the 7700 apparatus from ABI. The amplification was carried out in each case in duplicate. The means of the ct values obtained are formed, and the standard deviation is determined. The ct value can be used for the relative quantification of the transcript quantity in the RNA employed. The results are shown in table 7.

TABLE 7

| Composition | RANTES ct | RANTES Std. dev. | c-jun ct | c-jun Std. dev. |
|---|---|---|---|---|
| 1,2,4-Butanetriol | 25.23 | 0.05 | 25.40 | 0.14 |
| 3-Methyl-1,3,5-pentanetriol | 25.28 | 0.10 | 25.45 | 0.01 |
| 75% 1,2,3-propanetriol + 25% 1,2,6-hexanetriol | 25.17 | 0.10 | 25.64 | 0.09 |
| 1,2,6-hexanetriol | 24.95 | 0.02 | 25.53 | 0.03 |
| Control | 25.03 | 0.00 | 25.61 | 0.05 |

It can be seen from table 7 that the RNA which can be isolated from the samples treated in accordance with the invention is also well suited to downstream analyses.

10. RNA Analysis of Frozen Samples which have Been Treated in Accordance with the Invention Immediately after the removal of organs, rat liver tissue was frozen in liquid nitrogen and then stored in liquid nitrogen. In each case 20 to 50 mg of these samples were then incubated with in each case 1 ml of the compositions given in table 8 and stored for three days at 4 to 8° C. Thereafter, the RNA was isolated from the samples pretreated thus, as described in example 2. The result is shown in table 8.

It can be seen from table 8 that the method according to the invention is not only suitable for stabilizing fresh biological samples, but also for preparing frozen samples for the analysis of biomolecules.

TABLE 8

| Composition | RNA quantity [µg] |
|---|---|
| 1,3-Propanediol | 55.5 |
| 1,4-Butanediol | 55.2 |
| 1,3-Butanediol | 53.1 |
| Dipropylene glycol | 60.8 |
| Triethylene glycol | 65.6 |
| 50% Triethylene glycol + 50% 1,3-propanediol | 51.1 |
| 1,2,6-Hexanetriol | 46.7 |
| 1,2,3-Propanetriol | 49.3 |
| 1,7-Heptanediol | 53.5 |
| 1,5-Pentanediol | 48.3 |
| 1,6-Hexanediol | 51.7 |
| 2,4-Pentanediol | 45.4 |
| 2-Ethyl-2-(hydroxymethyl)-1,3-propanediol | 50.3 |
| 3-Allyoxy-12-propanediol | 40.4 |
| Cis-2-Butene-1,4-diol | 35.0 |

11. Induction Analysis of Samples Treated in Accordance with the Invention

The taking of a biological sample from the organism triggers a stress reaction in the cells. The gene expression profile immediately starts changing, firstly by RNA degradation, but secondly also by the induction of the synthesis of new transcripts. The treatment according to the invention of a biological sample must therefore prevent not only the degradation, but also the induction. To detect the immediate prevention of induction by treatment of the sample in accordance with the invention, rat lung tissue immediately after the removal of organs is treated with 1 ml of a composition consisting of 25% of 3-methyl-1,3,5-pentanetriol and 75% of 1,2,6-hexanetriol and stored for 2 h, 4 h and 24 h at 25° C. Tissue samples treated with PBS and stored identically, and tissue samples which, after the removal of organs, are immediately frozen in liquid nitrogen and stored at −80° C. act as the controls.

Thereafter, the RNA is isolated in accordance with the method described in example 2.

To carry out the further analysis of the isolated RNA, in each case 50 ng of total RNA in a total volume of 25 µl with a suitable mastermix for real-time RT-PCR, for example the Quantitect SYBRGreen RT-PCR kit from QIAGEN, is employed in accordance with the manufacturer's instructions. The amplification was carried out in a suitable real-time amplification apparatus, for example the 7700 apparatus from ABI. The amplification was carried out in each case in duplicate. The means of the ct values obtained are formed, and the standard deviation is determined. The ct value can be used for the relative quantification of the transcript quantity in the RNA employed. To this end, not only the target transcript, but also a transcript which has not been induced by stress is amplified for each sample as the endogenous control, in the present case GAPDH. The amount of the transcript to be tested is related to the detected amount of the control transcript, and the change in the quantity of the transcript to be tested in comparison with the control which has been frozen in liquid nitrogen is determined with the aid of the delta-delta-ct method (calculation as specified by the equipment manufacturer ABI). The immediate freezing in liquid nitrogen prevents any induction or degradation of transcripts, so that this sample represents the reference (time 0). The change in the transcript quantity during the storage of the sample in PBS or the composition according to the invention was determined mathematically and graphically. It becomes clear that storage in PBS induces the transcription of the c-fos gene and that, as a consequence, the quantity of the c-fos transcript increases markedly. When the sample is treated in accordance with the invention, however, the induction is suppressed successfully.

The invention claimed is:

1. A method of stabilizing a biological sample, comprising:
   i) providing a biological sample, and
   ii) contacting the biological sample with a composition comprising:
      ($\alpha$1) from 1 to 100% by weight of at least one polyol selected from the group consisting of a diol, triol, tetraol, pentaol, hexaol, heptoal, octoal, and nonaol, and
      ($\alpha$2) from 0 to 99% by weight of an additive selected from the group consisting of monohydric alcohols (monools), ketones, dimethyl sulfoxide, aromatic hydrocarbons, halogenated hydrocarbons, ethers, carboxylic acids, carboxamides, nitriles, nitroalkanes and esters,
   wherein the total weight % of components ($\alpha$1) and ($\alpha$2) in said composition amounts to 100% by weight.

2. The method as claimed in claim 1, wherein the biological sample is a frozen biological sample, 3. The method as claimed in claim 1, wherein the biological sample is a nonfrozen biological sample.

4. The method as claimed in claim 1, wherein the polyol is a diol or triol.

5. The method as claimed in claim 1, wherein the polyol comprises from 2 to 20 carbon atoms.

6. The method as claimed in claim 1, wherein the polyol is selected from the group consisting of 1,2-ethanediol, 1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, 1,2,3-propanetriol, 1,2,3-butanetriol, 1,2,4-butanetriol, 1,2,3-pentanetriol, 1,2,4-pentanetriol, 1,2,5-pentanetriol, 2,3,4-pentanetriol, 1,2,3-hexanetriol, 1,2,4-hexanetriol, 1,2,5-hexanetriol, 1,2,6-hexanetriol, 2,3,4-hexanetriol, 2,3,5-hexanetriol and 3-methyl-1,3,5-pentanetriol.

7. The method as claimed in claim 1, wherein the polyol comprises a mixture of at least two polyols.

8. The method as claimed in claim 1, wherein the contacting of the biological sample with the composition is carried out at a temperature in a range of from −80° C. to +80° C.

9. The method as claimed in claim 1, wherein the contacting of the biological sample with the composition is carried out at a temperature in the range of from 0° C. to +80° C.

10. The method as claimed in claim 1, wherein the method further comprises:
    iii) storing the sample at a temperature in the range of from −80° C. to +80° C.

11. The method as claimed in claim 10, wherein the biological sample is stored at a temperature in the range of from −0° C. to +80° C.

12. A method treating a biological sample according to claim 1 further comprising:
    iv) preparing the sample for histological analysis, or analysis of biomolecules in, or from, the biological sample.

13. The method as claimed in claim 12, wherein step iv) comprises both the histological analysis of the sample and the analysis of the biomolecules.

14. The method as claimed in claim 12, wherein step iv) comprises both the analysis of proteins and the analysis of nucleic acids.

15. The method as claimed in claim 12, wherein the biological sample is selected from the group consisting of organisms, isolated cells, organelles, bacteria, fungi, parts of fungi, viruses, viroids, prions, tissue, tissue fragments, tissue sections, body fluids, natural or optionally isolated proteins, synthetic or modified proteins, natural or optionally isolated nucleic acids, synthetic or modified nucleic acids, lipids, carbohydrates, metabolic products, metabolites, plants, parts of plants, fecal matter, smears, tap fluids, food samples, environmental samples, and forensic samples, 16. The method as claimed in claim 1, wherein the polyol comprises a mixture of at least two triols.

17. The method as claimed in claim 1, wherein the polyol consists of a mixture of two trials.

18. The method as in claim 1, wherein the polyol comprises a $C_3$-$C_7$ polyol.

19. The method as in claim 1, wherein the polyol comprises a $C_5$-$C_6$ polyol.

20. The method as in claim 1, wherein the polyol comprises a hexanetriol.

21. The method as in claim 1, wherein the polyol comprises a pentanetriol.

22. The method of claim 1, wherein the polyol comprises a mixture of a hexanetriol and a pentanetriol.

23. The method of claim 1, wherein the polyol comprises 1,2,6-hexanetriol.

24. The method of claim 1, wherein the polyol comprises 3-methyl-1,3,5-pentanetriol.

25. The method of claim 1, wherein the polyol comprises a mixture of 1,2,6-hexanetriol and 3-methyl-1,3,5-pentanetriol.

26. The method of claim 1, wherein the polyol comprises a mixture of 1,2,3-propantriol and 1,2,6-hexanetriol.

27. The method of claim 1, wherein the polyol comprises a mixture of 1,2,3-propantriol and 3-methyl-1,3,5-pentanetriol.

28. The method of claim 1, wherein the polyol comprises heptanetriol.

29. The method of claim 1, wherein the polyol comprises a mixture of 3-oxapentan-1,5-diol and 1,2,6-hexanetriol.

* * * * *